(12) United States Patent
Jin et al.

(10) Patent No.: US 10,506,810 B2
(45) Date of Patent: Dec. 17, 2019

(54) SYNERGISTIC HERBICIDAL COMPOSITION

(71) Applicant: QINGDAO KINGAGROOT RESISTANT WEED MANAGEMENT CO., LTD., Qindao, Shandong (CN)

(72) Inventors: Tao Jin, Shandong (CN); Jinxin Wang, Shandong (CN); Xingtao Lu, Shandong (CN); Xuegang Peng, Shandong (CN); Jingyuan Zhang, Shandong (CN); De Zhao, Shandong (CN)

(73) Assignee: QINGDAO KINGAGROOT RESISTANT WEED MANAGEMENT CO., LTD., Qingdao, Shandong (CN)

(*) Notice: Subject to any disclaimer, the term of this patent is extended or adjusted under 35 U.S.C. 154(b) by 0 days.

(21) Appl. No.: 15/775,868

(22) PCT Filed: Mar. 31, 2016

(86) PCT No.: PCT/CN2016/077953
§ 371 (c)(1),
(2) Date: May 14, 2018

(87) PCT Pub. No.: WO2017/084233
PCT Pub. Date: May 26, 2017

(65) Prior Publication Data
US 2018/0325113 A1    Nov. 15, 2018

(30) Foreign Application Priority Data
Nov. 17, 2015  (CN) .......................... 2015 1 0791710

(51) Int. Cl.
| | | |
|---|---|---|
| *A01N 43/56* | (2006.01) | |
| *A01N 25/04* | (2006.01) | |
| *A01N 25/32* | (2006.01) | |
| *A01N 35/10* | (2006.01) | |
| *A01N 37/26* | (2006.01) | |

(Continued)

(52) U.S. Cl.
CPC ............. *A01N 43/56* (2013.01); *A01N 25/04* (2013.01); *A01N 25/32* (2013.01); *A01N 35/10* (2013.01); *A01N 37/26* (2013.01); *A01N 37/34* (2013.01); *A01N 37/40* (2013.01); *A01N 37/48* (2013.01); *A01N 39/02* (2013.01); *A01N 43/40* (2013.01); *A01N 43/653* (2013.01); *A01N 43/70* (2013.01); *A01N 43/707* (2013.01); *A01N 43/78* (2013.01); *A01N 43/82* (2013.01); *A01N 43/88* (2013.01); *A01N 43/90* (2013.01); *A01N 47/30* (2013.01); *A01N 47/36* (2013.01); *A01N 47/38* (2013.01); *A01N 2300/00* (2013.01)

(58) Field of Classification Search
USPC ........................................................ 504/132
See application file for complete search history.

(56) References Cited

U.S. PATENT DOCUMENTS

| 4,643,757 | A | 2/1987 | Baba et al. |
| 5,998,334 | A | 12/1999 | Murai et al. |
| 2002/0065200 | A1 | 5/2002 | Schmitt et al. |

FOREIGN PATENT DOCUMENTS

| CN | 1216535 A | 5/1999 |
| CN | 1422258 A | 6/2003 |

(Continued)

OTHER PUBLICATIONS

Metwally et al. (Journal of American Science, 2010; 6(11).*

(Continued)

*Primary Examiner* — Johann R Richter
*Assistant Examiner* — Courtney A Brown
(74) *Attorney, Agent, or Firm* — Leydig Voit & Mayer Ltd.

(57) ABSTRACT

The present invention belongs to the technical field of synergistic pesticides, and particularly relates to a synergistic herbicidal composition comprising a 4-benzoylpyrazole compound. The synergistic herbicidal composition comprises an active ingredient A and an active ingredient B in an herbicidally effective amount, wherein, the active ingredient A is the compound of

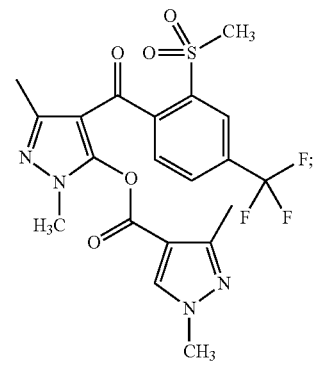

the active ingredient B is one or more compounds selected from: 1) a phenoxycarboxylic acid; 2) a pyridinecarboxylic acid; 3) a benzoic acid; 4) a hydroxybenzonitrile; 5) an urea; 6) a pyridine; 7) a triazolinone; 8) a diphenyl ether; 9) an acetamide; 10) an aryloxyphenoxypropionate; 11) a cyclohexanedione; 12) a sulfonylurea; 13) a triazine; 14) a sulfonamide; 15) a phenylpyrazoline; and 16) others: bentazon. The composition is effective for controlling a broadleaved weed in wheat fields, has extended weed-controlling spectrum, significant synergistic effect and reduced application rate, and is safe for a crop.

16 Claims, No Drawings

(51) Int. Cl.
    *A01N 37/34*     (2006.01)
    *A01N 37/40*     (2006.01)
    *A01N 37/48*     (2006.01)
    *A01N 39/02*     (2006.01)
    *A01N 43/40*     (2006.01)
    *A01N 43/653*     (2006.01)
    *A01N 43/70*     (2006.01)
    *A01N 43/707*     (2006.01)
    *A01N 43/78*     (2006.01)
    *A01N 43/82*     (2006.01)
    *A01N 43/88*     (2006.01)
    *A01N 43/90*     (2006.01)
    *A01N 47/30*     (2006.01)
    *A01N 47/36*     (2006.01)
    *A01N 47/38*     (2006.01)

(56) References Cited

FOREIGN PATENT DOCUMENTS

| CN | 103980202 A | * | 8/2014 |
|---|---|---|---|
| CN | 103980202 A | | 8/2014 |
| CN | 105230629 A | | 1/2016 |
| CN | 105685049 A | | 6/2016 |
| WO | WO 2017/084233 A1 | | 5/2017 |

OTHER PUBLICATIONS

International Bureau, International Search Report in International Application No. PCT/CN2016/077953, dated Aug. 23, 2016.
European Patent Office, Extended European Search Report in European Application No. 16865416.8, dated Oct. 7, 2018.

* cited by examiner

SYNERGISTIC HERBICIDAL COMPOSITION

CROSS-REFERENCE TO RELATED APPLICATIONS

This patent application is the U.S. National Stage of International Patent Application No. PCT/CN2016/077953, filed Mar. 31, 2016, which claims the benefit of Chinese Patent Application No. 201510791710.5, filed Nov. 17, 2015, which are each incorporated by reference.

TECHNICAL FIELD

The present invention belongs to the technical field of synergistic pesticides, and particularly relates to a synergistic herbicidal composition comprising a 4-benzoylpyrazole compound.

BACKGROUND ART

Chemical control of weed with herbicide(s) is a most economical and effective means for controlling weeds in farmlands. However, continuously use of a single chemical herbicide or chemical herbicides having a single functional mechanism at a high dosage for a long period of time is likely to cause problems associated with evolved drug resistance and tolerance of weeds. Well complexing or formulating of herbicidal compounds can achieve the following advantages: expanding weed spectrum, improving weed control effect, and delaying occurrence and development of drug resistance and tolerance of weeds, and thus is one of the most effective means to solve the above problems.

The hydroxyphenyl pyruvate dioxygenase (HPPD) inhibitor is another novel herbicide following the acetyl CoA carboxylase (ACCase) inhibitor, the acetolactate synthase (ALS) inhibitor and the Protox inhibitor etc. The HPPD inhibitor has a broad spectrum of herbicidal activity, can be used before and after budding, and may cause albinism and death of weeds. Although the HPPD inhibitor result in similar poisoning symptoms to that of carotenoid bio-inhibitors, it is markedly different from the known carotenoid bio-inhibitors in terms of chemical properties such as polarity and ionization degree etc. . . . . . The risk of resistance of weeds to HPPD inhibitor herbicides is significantly reduced compared to that of ACCase inhibitors and ALS inhibitors, and there is no cross target resistance resulted from a HPPD inhibitor and a common ALS inhibitor (e.g., tribenuron, bensulfuron-methyl, florasulam) which is usually used in wheat fields.

Herbicides, such as protoporphyrinogen oxidase (PPO) inhibitors, photosynthetic photosystem II herbicides and phytoene dehydrogenase (PDS) inhibitors, play an important role in a system for preventing the growth of weeds in wheat fields.

Conventional photosynthetic photosystem II herbicides in wheat fields comprise bromoxynil, octanoylbromobenzonitrile, iodobenzonitrile, bentazone, isoproturon, chlorotoluron, terbutryn, prometryn, metribuzin, and the like; photosynthetic photosystem II herbicides are selective contact herbicides acting on stems and leaves after budding, and mainly absorbed by the leaves and rapidly result in tissue necrosis by inhibiting each step in photosynthesis. The above herbicides can be used for controlling broad-leaved weeds in wheat fields, such as *Sisymbrium sophia, Capsella bursa-pastoris,* and *Catchweed* etc. However, when this class of herbicides is used alone, a high dosage is needed, and the wheat is at serious safety risk. If they are used at a low dosage, the weed control effect is poor. Therefore, it is required strict application technique and dosage. There is no cross target resistance resulted from a photosynthetic photosystem II herbicide and a common ALS inhibitor (e.g., tribenuron, bensulfuron-methyl, florasulam) which is usually used in wheat fields.

Conventional phytoene dehydrogenase (PDS) inhibitors in wheat fields comprise diflufenican, picolinafen, and the like. This class of herbicides belongs to carotenoid biosynthetic inhibitors, which lead to chlorophyll damage and cell rupture, and plant death, is a broad-spectrum selective herbicides in wheat fields and suitable for controlling broad-leaved weeds in barley and wheat fields, such as *Sisymbrium sophia, Capsella bursa-pastoris, Catchweed*, and *Myosoton aquaticum* etc. However, when this class of agents is used alone, a high dosage is needed, and the wheat is at serious safety risk. If they are used at a low dosage, the weed control effect is poor. Therefore, it is required strict application technique and dosage. There is no cross target resistance resulted from a PDS inhibitor and a common ALS inhibitor (e.g., tribenuron, bensulfuron-methyl, florasulam) which is usually used in wheat fields.

THE CONTENTS OF THE INVENTION

In order to solve the above existing problems in the prior art, the present invention provides a synergistic herbicidal composition comprising 4-benzoylpyrazole compound. The composition is effective in controlling a broad-leaved weed in wheat fields, and is characterized by having extended weed-controlling spectrum, significant synergistic effect and reduced application rate, and being safe for crops.

The present application provides a synergistic herbicidal composition, comprising an active ingredient A and an active ingredient B in an herbicidally effective amount, wherein, the active ingredient A is

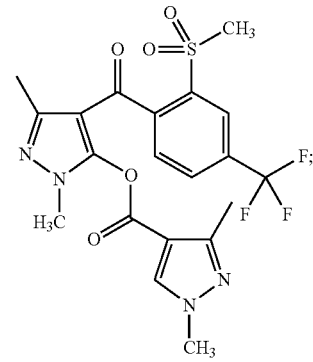 [SMILES: Cc1nn(C)cc1C(=O)Oc1c(C(=O)c2ccc(C(F)(F)F)cc2S(C)(=O)=O)c(C)nn1C]

the active ingredient B is one or more compounds selected from:

1) a phenoxycarboxylic acid: 2-methyl-4-chlorophenoxy acetic acid (MCPA), MCPA-thioethyl, MCPB, mecoprop, MCPA-Na, MCPA-isooctyl, 2,4-dichlorophenoxyacetic acid (2,4-D), 2,4-D butyl ester, 2,4-D isooctyl ester, 2,4-DB, or 2-(2,4-Dichlorophenoxy)propionic acid;

2) a pyridinecarboxylic acid: fluroxypyr, fluroxypr-mepthyl, halauxifen-methyl, triclopyr, or clopyralid;

3) a benzoic acid: dicamba;

4) a hydroxybenzonitrile: bromoxynil, bromoxynil octanoate, or ioxynil;

5) an urea: isoproturon or chlorotoluron;

6) a pyridine: diflufenican or picolinafen;

7) a triazolinone: carfentrazone;

8) a diphenyl ether: fluoroglycofen;

9) an acetamide: acetochlor, flufenacet, mefenacet, metolachlor, or napropamid;

10) an aryloxyphenoxypropionate: fenothiocarb, clodinafop, or clodinafop-propargyl;

11) a cyclohexanedione: tralkoxydim;

12) a sulfonylurea: tribenuron, bensulfuron-methyl, thifensulfuron, halosulfuron-methyl, mesosulfuron-methyl, sulfosulfuron, propoxycarbazone, or flucarbazone-sodium;

13) a triazine: metribuzin, prometryn, terbutryn;

14) a sulfonamide: florasulam, flumetsulam, or pyroxsulam;

15) a phenylpyrazoline: pinoxaden; and 16) others: bentazon.

Preferably, the active ingredient B is one or more compounds selected from a group consisting of 2-methyl-4-chlorophenoxy acetic acid (MCPA), MCPA-Na, MCPA-isooctyl, 2,4-D butyl ester, 2,4-D isooctyl ester, fluroxypyr, fluroxypr-mepthyl, halauxifen-methyl, isoproturon, diflufenican, picolinafen, carfentrazone, fluoroglycofen, fenothiocarb, clodinafop, clodinafop-propargyl, tralkoxydim, halosulfuron-methyl, mesosulfuron-methyl, flucarbazone-sodium, metribuzin, prometryn, terbutryn, florasulam, pyroxsulam, pinoxaden, bentazon, bromoxynil, bromoxynil octanoate, and chlorotoluron.

Preferably, the weight ratio of the actice ingredient A to the actice ingredient B is 1-100: 1-100, preferably the weight ratio of the actice ingredient A to the actice ingredient B is 1-80, 1-50: 1-50, or 1-30: 1-30, more preferably, the weight ratio of the actice ingredient A to the actice ingredient B is 1-20: 1-20, or 1-10: 1-10. A synergistic effect can be achieved by mixing the active ingredient A with the active ingredient B within the defined weight ratio ranges.

The active ingredients A and B together account for 1-95%, preferably 10-80% of the total weight of the synergistic herbicidal composition. In general, the herbicidal composition of the present invention comprises from 1 to 95 parts by weight of the active ingredients and from 5 to 99 parts by weight of a conventional pesticide adjuvant.

The conventional adjuvant in the composition according to the invention may be a carrier, a surfactant and the like.

The term "carrier" herein refers to an organic or inorganic, natural or synthetic substance, which facilitates the application of the active ingredients. In general, the carrier is inert and must be agriculturally acceptable, especially is acceptable to a plant to be treated. The carrier may be a solid, such as clay, a natural or synthetic silicate, silica, a resin, a wax, a solid fertilizer and so on; or a liquid such as water, an alcohol, a ketone, a petroleum fraction, an aromatic or paraffinic hydrocarbon, a chlorohydrocarbon, liquefied gas and so on.

The surfactant, which may be ionic or non-ionic, can include an emulsifier, a dispersant or a wetting agent. Examples which may be mentioned are a salt of polyacrylic acid, a salt of lignosulfonic acid, a salt of phenolsulfonic acid or of naphthalenesulfonic acid, a polymer of ethylene oxide with an aliphatic alcohol or with an aliphatic acid or with an aliphatic amine or with a substituted phenol (in particular, an alkylphenol or an arylphenol), a sulfosuccinate, a taurine derivative (especially an alkyl taurate) and a phosphoric ester of an alcohol or of a polyhydroxyethylated phenol, an alkyl sulfonate, an alkylaryl sulfonate, an alkyl sulfate, a laurylether sulfate, a fatty alcohol sulfate, a sulfated hexadecanol, heptadecanol and octadecanol and a sulfated fatty alcohol polyglycol ether, and further include a condensate of naphthalene or naphthalenesulfonic acid with phenol and formaldehyde, polyoxyethylene octylphenyl ether, ethoxylated isooctylphenol, octylphenol or nonylphenol, a polyethylene glycol alkylphenyl ether, a polyethylene glycol tributylphenyl ether, a polyethylene glycol tristearylphenyl ether, a alkylaryl polyether alcohol, an alcohol and fatty alcohol/ethylene oxide condensate, ethoxylated castor oil, a polyoxyethylene alkyl ether, an ethoxylated polyoxypropylene, a lauryl alcohol polyglycol ether acetal, a sorbitol ester, a lignin sulfite waste liquid, a protein, a denatured protein, a polysaccharide (e.g., methylcellulose), a hydrophobic modified starch, a polyvinyl alcohol, a polycarboxylate, a polyalkoxylate, a polyvinylamine, a polyvinylpyrrolidone, and a copolymer thereof. At least one surfactant may be required to facilitate dispersion of the active ingredient in water and proper application thereof to a plant.

The composition can also comprise various other components, such as a protective colloid, an adhesive, a thickener, a thixotropic agent, a penetrant, a stabilizer, a chelating agent, a dye, a colorant or a polymer.

The composition of the present invention may be diluted prior to use or used directly by users. The compositon can be prepared through a conventional processing method, that is, the active ingredient(s) is mixed with a liquid solvent or a solid carrier, and then one or more of the surfactants such as a dispersant, a stabilizer, a wetting agent, an adhesive, or a defoaming agent, etc. are added.

A specific formulation of the herbicidal composition may be an emulsifiable concentrate, a suspension, a microemulsion, a suspoemulsion, an aqueous emulsion, a dispersible oil suspension, a wettable powder or a water-dispersible granule (a dry suspension).

When the composition is formulated into a wettable powder, the composition comprises the following components: 1% to 70% of the active ingredient A, 1% to 50% of the active ingredient B, 5% to 10% of the dispersant, 2% to 10% of the wetting agent, and balanced with a filler.

The active ingredient A, the active ingredient B, the dispersant, the wetting agent and the filler are mixed uniformly in a mixing tank, then subjected to air-jet mill and mixed uniformly again to prepare the wettable powder of the composition of the present invention.

When the composition is formulated into a water-dispersible granule, the composition comprises the following components: 1% to 70% of the active ingredient A, 1% to 50% of the active ingredient B, 3% to 12% of the dispersant, 1% to 8% of the wetting agent, 1%-10% of a disintegrant, 1%-8% of the adhesive, and balanced with a filler.

The active ingredient A, the active ingredient B, the dispersant, the wetting agent, the disintegrant, the filler and the like are subjected to air-jet mill to reach a desired particle size, then the adhesive and other adjuvants are added to get a material for the granulation. The material is quantitatively fed into a fluidized-bed granulation dryer for granulation and drying, thereby affording the water-dispersible granule of the composition of the present invention.

When the composition is formulated into a suspension, the composition comprises the following components: 0.1% to 40% of the active ingredient A, 0.1% to 30% of the active ingredient B, 2% to 10% of the dispersant, 2% to 10% of the wetting agent, 0.1% to 1% of the defoaming agent, 0.1% to 2% of the thickener and 0.1% to 8% of an antifreezing agent, and balanced with deionized water.

The dispersant, the wetting agent, the defoaming agent, the thickener and the antifreezing agent in the above formula are mixed uniformly under high-speed shear, then added with the active ingredient A and the active ingredient B, and subjected to a ball mill for 2 to 3 hours to allow the particle size of all particles below 5 μm to prepare the suspension of the composition of the invention.

When the composition is formulated into a suspoemulsion, the composition comprising the following components: 0.1% to 40% of the active ingredient A, 0.1% to 30% of the active ingredient B, 2% to 12% of the emulsifier, 2% to 10% of the dispersant, 0.1% to 2% of the defoaming agent, 0.1% to 2% of the thickener, 0.1% to 8% of the antifreezing agent, 0.05% to 3% of the stabilizer, and balanced with water.

The dispersant, the defoaming agent, the thickener, the antifreezing agent and the stabilizer in the above formula are mixed uniformly under high-speed shear, then added with the active ingredient B technical material, and subjected to a ball mill for 2 to 3 hours to allow the particle size of all particles below 5 μm to prepare a suspension of the active ingredient B, and the active ingredient A technical material, the emulsifier and other adjuvants are directly emulsified into the suspension by using a high-speed stirrer to obtain the suspoemulsion of the composition of the present invention.

When the composition is formulated into an aqueous emulsion, the composition comprises the following components: 0.1% to 40% of the active ingredient A, 0.1% to 30% of the active ingredient B, 2% to 10% of a solvent, 2% to 12% of the emulsifier, 2% to 10% of the dispersant, 0.2% to 5% of an co-emulsifier, 0.1% to 8% of the antifreezing agent, 0.1% to 2% of the defoaming agent, 0.1% to 2% of the thickener, and balanced with deionized water.

The technical material, the solvent, the emulsifier and the co-emulsifier in the above formula are added together and dissolved into a homogeneous oil phase. The deionized water, the dispersant, the antifreezing agent, the defoaming agent, the thickener are mixed together into a homogeneous aqueous phase, and the aqueous phase is slowly dropped into the oil phase under high-speed stirring to prepare the well dispersed aqueous emulsion of the composition of the present invention.

When the composition is formulated into a microemulsion, the composition comprises the following components: 0.1% to 40% of the active ingredient A, 0.1% to 30% of the active ingredient B, 5% to 15% of the emulsifier, 2% to 10% of solvent, 5% to 10% of the antifreezing agent, 0.5% to 3% of the stabilizer, and balanced with deionized water.

The technical material, the solvent and the emulsifier in the above formula are added to a container for preparing a mother liquor to prepare a homogenous oil phase, then uniformly mixed with the deionized water and the antifreezing agent, etc., and injected into a container for preparing product and mixed under high-speed stirring to prepare the transparent or semitransparent microemulsion of the composition of the present invention.

In short, the composition of the present invention can be mixed with solid and liquid additives conventionally used in formulations of the prior art.

In a further preferred embodiment, the herbicidal composition further comprises a safener C, which is one or more compounds selected from the group consisting of mefenpyrdiethyl, cloquintocet-methyl, isoxadifen-ethyl, cyprosulfamide, naphthalic anhydride (NA), Dichlormid, R-28725, AD-67, CGA-154281 (Benoxacor), CGA-43089 (Cyometrinil), CGA-43089 (Cyometrinil), Hoe-70542 (Fenchlorazole), Fenclorim, Flurazole, BAS-145138, MON-13900, quinoline derivatives, sulfonylurea (sulfamide) safeners, 2,4-D (organic acids), new antidote T (4% $Ti^{4+}$ as a main component) and gibberellin (GA).

The composition according to the invention can be sprayed to a leaf of a plant to be treated, i.e., the composition of the invention can be applied to a weed, especially to the weed which is harmful to the growth of crops, and particularly to a surface of the weed from where the weed invades or is likely to invade crops, and the active ingredients are usually applied at a dosage of 15-1500 g/ha, preferably 30-750 g/ha.

A 2-year field efficacy test of the composition of the present invention shows that, from 3-leaf stage to greening stage of wheats, and from 1-leaf stage to 5-leaf stage of a weed, there is no pesticide toxicity to wheats from the application to mature stage. The result indicates the composition is safe for wheats. The weed control effect is more than 90% after 45 days. With the increase in dosage, the control effect is increased significantly. Weeds can be well controlled in the whole growing period of crops by administration of the composition for only once, which not only leads to a remarkable weed control effect but also is environment-friendly, without affecting the next crops.

When the herbicidal composition of the present invention is applied, an unexpected synergistic effect is achieved, and the herbicidal activity is greater than a single or the sum of the predicted activity of each herbicide. The synergistic effect is manifested by a reduced application rate, a broader weed control spectrum, and faster and more durable weeding action, all of which are required for weed control practices. In regarding to the described characteristics, the composition is significantly superior to the existing herbicides in the art.

The herbicidal composition of the present invention also has following advantages:

(1) The composition of the present invention is environmentally friendly, which is easily degraded in the environment and is safe for both current wheat and succeeding crops.

(2) The herbicidal composition of the invention is of low cost and convenient in usage, and has great economic and social benefit for popularization and application thereof.

(3) Compared with those in the prior art, the herbicidal composition of the present invention not only can control non-resistant broad-leaved weeds but also can control broad-leaved weeds that are resistant to ALS inhibitors, and thus is an effective solution for solving weed resistance in wheat fields.

SPECIFIC MODE FOR CARRYING OUT THE INVENTION

The following examples provided are not intend to limit the invention, but merely to illustrate how the invention is carried out. These examples show particularly significant effectiveness to certain weeds.

A. EXAMPLES

1) Emulsifiable Concentrates (ECs)

1.1) Active ingredients were A and B, wherein the active ingredient B was fluoroglycofen.

The formulation consisted of: 2.5% A+0.5% fluoroglycofen+5% cyclohexanone+5% calcium dodecylbenzenesulfonate+5% phenylethyl phenol polyoxyethylene ether+balanced with 100# aromatic solvent naphtha.

1.2) Active ingredients were A and B, wherein the active ingredient B was 2,4-D butyl ester.

The formulation consisted of: 2.5% A+23% 2,4-D butyl ester+10% isopropanol+4% calcium dodecylbenzenesulfonate+6% polyoxyethylene castor oil+balanced with 150# aromatic solvent naphtha.

1.3) Active ingredients were A and B, wherein the active ingredient B was bromoxynil octanoate.

The formulation consisted of: 2.5% A+25% bromoxynil octanoate+5% N-methylpyrrolidone+4% calcium dodecylbenzenesulfonate+5% fatty alcohol ethoxylate+balanced with 100 # aromatic solvent naphtha.

1.4) Active ingredients were A and B, wherein the active ingredient B was 2,4-D isooctyl ester.

The formulation consisted of: 2.5% A+25% 2,4-D isooctyl ester+5% cyclohexanone+4% calcium dodecylbenzenesulfonate+6% nonylphenol polyoxyethylene ether+balanced with 100# aromatic solvent naphtha.

The equipments for processing the above emulsifiable concentrates: a vacuum pump, a mixing tank, and a storage tank.

The process for processing the above emulsifiable concentrates: all materials were fed into the mixing tank, dissolved under stirring to completely transparent, and transferred to the storage tank after passing the inspection.

2) Microemulsions 2.1) Active ingredients were A and B, wherein the active ingredient B was fluroxypyr.

The formulation consisted of: 5% A+12% fluroxypyr+10% cyclohexanone+10% ethanol+8% sodium diethylhexyl sulfosuccinate+8% phenylethyl phenol polyoxyethylene ether+3% phenylethyl phenol polyoxyethylene formaldehyde resin condensate+balanced with water.

2.2) Active ingredients were A and B, wherein the active ingredient B was fenothiocarb.

The formulation consisted of: 2.5% A+6% fenothiocarb+6% cyclohexanone+6% 150# solvent naphtha+10% ethanol+8% calcium dodecylbenzenesulfonate+8% nonylphenol polyoxyethylene ether+5% phenylethyl phenol polyoxyethylene ether formaldehyde resin condensate+balanced with water.

2.3) Active ingredients were A and B, wherein the active ingredient B was clodinafop.

The formulation consistes of: 4% A+10% clodinafop+10% cyclohexanone+10% ethylene glycol butyl ether+8% calcium dodecylbenzenesulfonate+8% polyoxyethylene castor oil+5% phenylethyl phenol polyoxyethylene ether formaldehyde resin condensate+balanced with water.

2.4) Active ingredients were A and B, wherein the active ingredient B was pinoxaden.

The formulation consisted of: 5% A+12% pinoxaden+10% cyclohexanone+5% 150# solvent naphtha+10% ethylene glycol butyl ether+8% calcium dodecylbenzenesulfonate+8% fatty alcohol ethoxylate+5% phenylethyl phenol polyoxyethylene ether formaldehyde resin condensate+balanced with water.

The equipments for processing the above microemulsions: a vacuum pump, a mixing tank, and a storage tank.

The process for processing the above microemulsions: the technical material and the solvent were fed into the mixing tank, and dissolved under stirring to completely transparent; the emulsifier was added and stirred uniformly; water was finally added, and the stirring was continued until the solution was completely transparent; after passing the inspection, the solution was transferred to the storage tank.

3) Aqueous Emulsions 3.1) Active ingredients were A and B, wherein the active ingredient B was MCPA-isooctyl.

The formulation consisted of: 2.5% A+24.5% MCPA-isooctyl+5% cyclohexanone+3% phenylethyl phenol polyoxyethylene ether phosphate triethanolamine salt+2% phenylethyl phenol polyoxyethylene ether+3% polyoxyethylene castor oil+3% ethylene glycol+balanced with water.

3.2) Active ingredients were A and B, wherein the active ingredient B was halauxifen-methyl.

The formulation consisted of: 2.5% A+0.5% halauxifen-methyl+10% cyclohexanone+10% 150# solvent naphtha+3% nonylphenol polyoxyethylene ether phosphate triethanolamine salt+2% phenylethyl phenol polyoxyethylene ether+3% polyoxyethylene castor oil+3% ethylene glycol+balanced with water.

The equipments for processing the above aqueous emulsions: a vaccum pump, a mixing tank, a storage tank, and a shear tank.

The process for processing the above aqueous emulsions: the technical materials and solvent were fed into the mixing tank and dissolved under stirring to completely transparent, and then the emulsifier was added and stirred uniformly to obtain the oil phase; ethylene glycol, the defoaming agent and water were drawn into the shear tank, and the oil phase was slowly drawn into the shear tank in shear state; after all materials were drawn into the tank, the shearing was continued for 1 hour; after passing the inspection, the product is transferred to the storage tank.

4) Suspensions 4.1) Active ingredients were A and B, wherein the active ingredient B was isoproturon.

The formulation consisted of: 1.5% A+33.5% isoproturon+5% sodium lignosulphonate+2% nekal+0.2% xanthan+5% glycerol+balanced with water.

4.2) Active ingredients were A and B, wherein the active ingredient B was terbutryn.

The formulation consisted of: 2.5% A+47.5% terbutryn+5% naphthalenesulfonate+2% fatty alcohol ethoxylate+0.1% xanthan+5% glycerol+balanced with water.

4.3) Active ingredients were A and B, wherein the active ingredient B was diflufenican.

The formulation consisted of: 5% A+30% diflufenican+5% nonylphenol polyoxyethylene ether phosphate triethanolamine salt+2% fatty alcohol ethoxylate+0.15% xanthan+5% glycerol+balanced with water.

4.4) Active ingredients were A and B, wherein the active ingredient B was picolinafen.

The formulation consisted of: 25% A+15% picolinafen+5% polycarboxylate dispersant+2% nonylphenol polyoxyethylene ether+0.2% xanthan+5% glycerol+balanced with water.

4.5) Active ingredients were A and B, wherein the active ingredient B was dimethylammonium 4-chloro-o-tolyloxyacetate.

The formulation consisted of: 2.5% A+19.5% dimethylammonium 4-chloro-o-tolyloxyacetate+5% polycarboxylate dispersant+2% fatty alcohol ethoxylate+0.3% xanthan+5% glycerol+balanced with water.

The equipments for processing the above suspensions: a mixing tank, a colloid mill, a sand mill, and a shearer etc.

The process for processing the above suspensions: all of the materials were fed into the mixing tank and mixed under stirring, introduced into the colloid mill, then subjected to 3-grade gringing in the sand mill, and finally sheared uniformly in the shearer, and transferred to the storage tank after passing the inspection.

5) Dispersible Oil Suspensions 5.1) Active ingredients were A and B, wherein the active ingredient B was bromoxynil.

The formulation consisted of: 2.5% A+17.5% bromoxynil+5% phenylethyl phenol polyoxyethylene ether phosphate triethanolamine salt+5% fatty acid polyoxyethylene ester+8% polyoxyethylene castor oil+2% organobentonite+balanced with methyl oleate.

5.2) Active ingredients were A and B, wherein the active ingredient B was bentazon.

The formulation consisted of: 1.5% A+36% bentazon+5% sodium diethylhexyl sulfosuccinate+5% nonylphenol polyoxyethylene ether+8% polyoxyethylene castor oil+0.5% organobentonite+balanced with methyl oleate.

5.3) Active ingredients were A and B, wherein the active ingredient B was isoproturon.

The formulation consisted of: 1.5% A+35% isoproturon+5% fatty alcohol ethoxylate phosphate triethanolamine salt+5% sorbitan polyoxyethylene ether fatty acid ester+2% polyoxyethylene castor oil+0.6% organobentonite+balanced with methyl oleate.

5.4) Active ingredients were A and B, wherein the active ingredient B was mesosulfuron-methyl.

The formulation consisted of: 5% A+1.8% mesosulfuron-methyl+5% sodium diethylhexyl sulfosuccinate+5% sorbitan polyoxyethylene ether fatty acid ester+6% castor oil polyoxyethylene+3% organobentonite+3% fumed silica+20% soybean oil+balanced with methyl oleate.

5.5) Active ingredients were A and B, wherein the active ingredient B was flucarbazone-sodium.

The formulation consisted of: 5% A+6% flucarbazone-sodium+5% fatty alcohol ethoxylate phosphate triethanolamine salt+5% fatty alcohol polyethylene ether+4% polyoxyethylene castor oil+3% organobentonite+20% soybean oil+balanced with methyl oleate.

5.6) Active ingredients were A and B, wherein the active ingredient B was florasulam.

The formulation consisted of: 5% A+1% florasulam+5% sodium diethylhexyl sulfosuccinate+5% sorbitan polyoxyethylene ether fatty acid ester+4% nonylphenol polyoxyethylene ether+2.6% organobentonite+25% soybean oil+balanced with methyl oleate 5.7) Active ingredients were A and B, wherein the active ingredient B was pyroxsulam.

The formulation consisted of: 2.5% A+0.9% pyroxsulam+5% fatty alcohol ethoxylate phosphate triethanolamine salt+5% sorbitan polyoxyethylene ether fatty acid ester+6% nonylphenol polyoxyethylene ether+3% organobentonite+25% soybean oil+balanced with methyl oleate.

The equipments for processing the above dispersible oil suspensions: a mixing tank, a colloid mill, a sand mill, and a shearer etc.

The process for processing the above dispersible oil suspensions: all of the materials were fed into the mixing tank and mixed under stirring, introduced into the colloid mill, then subjected to 3-grade gringing in the sand mill, and finally sheared uniformly in the shearer, and transferred to the storage tank after passing the inspection.

6) Wettable Powders 6.1) Active ingredients were A and B, wherein the active ingredient B was chlorotoluron.

The formulation consisted of: 1.5% A+50% chlorotoluron+10% sodium lignosulphonate+5% nekal+5% precipitated silica+balanced with diatomite.

6.2) Active ingredients were A and B, wherein the active ingredient B was prometryn.

The formulation consisted of: 3% A+30% prometryn+8% naphthalenesulfonate+5% fatty alcohol ethoxylate+5% precipitated silica+balanced with calcined kaolin.

6.3) Active ingredients were A and B, wherein the active ingredient B was MCPA-Na.

The formulation consisted of 5% A+35% MCPA-Na+6% polycarboxylate dispersant+5% fatty alcohol ethoxylate+5% precipitated silica+balanced with calcined kaolin.

The equipments for processing the above wettable powders: a mechanical mill, and a jet mill.

The process for processing the above wettable powders: the technical material, adjuvants, silica, and kaolin etc. were fed into the mechanical mill, then introduced into the jet mill, sampled, and detected, and qualified product was for future use.

7) Water-Dispersible Granules 7.1) Active ingredients were A and B, wherein the active ingredient B was carfentrazone.

The formulation consisted of: 2.5% A+0.5% carfentrazone+10% naphthalenesulfonate+5% nekal+1% polyvinyl alcohol as a disintegrant+balanced with diatomite as a filler.

7.2) Active ingredients were A and B, wherein the active ingredient B was metribuzin.

The formulation consisted of: 2.5% A+11.5% metribuzin+10% polycarboxylate+5% polyethylene glycol+1% polyvinyl alcohol as a disintegrant+balanced with diatomite as a filler.

7.3) Active ingredients were A and B, wherein the active ingredient B was MCPA.

The formulation consisted of: 2.5% A+16% MCPA+12% polycarboxylate+5% fatty alcohol ethoxylate+1% polyvinyl alcohol as a disintegrant+balanced with kaolin as a filler.

7.4) Active ingredients were A and B, wherein the active ingredient B was tralkoxydim.

The formulation consisted of: 5% A+60% tralkoxydim+15% polycarboxylate+5% nekal+1% polyvinyl alcohol as a disintegrant+balanced with bentonite as a filler.

7.5) Active ingredients were A and B, wherein the active ingredient B is halosulfuron-methyl.

The formulation consisted of: 15% A+24% halosulfuron-methyl+20% polycarboxylate+5% polyethylene glycol+1% polyvinyl alcohol as a disintegrant+balanced with diatomite as a filler.

The equipments for processing the above water-dispersible granules: a jet mill, a coulter type mixer, a basket granulator, a drying oven, and a screening device etc.

The process for processing the above water-dispersible granules: tha above materials were mixed uniformly, passed through the jet mill, kneaded by adding water and granulized, dried, and screened to obtain the product.

B. EFFICACY ASSAYS

1) Experimental Conditions 1.1) Tested Targets

*Capsella bursa-pastoris, Myosoton aquaticum, Alopecurus japonicus* were collected from corn fields in Huangdao Experimental Base of Shandong Province.

The above weeds were cultivated by a pot culture method. A 180 x140 mm plastic nutritional bowl contained 4/5 topsoil from the field was placed in an enamel pan, wherein the soil had been air-dried and screened and had an initial moisture content of 20%. Full and uniform weed seeds were selected, soaked in warm water at 25° C. for 6 hours, and germinated in a 28° C. biochemical incubator (darkness). The weed seeds that had just germinated were evenly placed on the surface of the soil and then covered with 0.7 cm soil, and cultured in a controllable sunlight greenhouse after being treated with agents. A certain amount of water was added to the enamel pan regularly to keep the soil moist.

1.2) Culture Conditions

The culture was carried out in a controllable sunlight greenhouse at 18 to 30° C., in natural light, and relative humidity of 57% to 72%.

The soil was loam with an organic matter content of 1.63%, a pH value of 7.1, an alkali-hydrolyzable nitrogen of 84.3 mg/kg, a rapidly available phosphorus of 38.5 mg/kg, and a rapidly available potassium 82.1 mg/kg.

1.3) Equipments and Apparatuses

3WP-2000-type Walking Spray Tower (Nanjing Institute of Agricultural Machinery, the Ministry of Agriculture); GA110-type ten thousandth Electronic Balance (Germany); ZDR2000-type Intelligent Data Recorder (Hangzhou Zeda Instrument Co., Ltd.); and SPX-type Intelligent Biochemical Incubator (Ningbo Jiangnan Instrument Factory).

2) Designs of Experiments 2.1) Reagents 2.1.1) Agents for the Experiment

The active ingredient B for use was commercially available technical material, the active ingredient A was the compound of the formula (I), which was produced by our company.

The technical materials were all dissolved in acetone, and diluted with an aqueous solution containing 0.1% emulsifier T-80. The dilution is performed as required.

2.2) Experimental Treatments 2.2.1) Determination of Dosage

A ratio of the active ingredient A to the active ingredient B and amounts thereof in each group depends on the characteristics and toxicity of the two agents, as well as the main application purpose of a corresponding formulation. Based on the pre-tests in this study, the dosage of the active ingredient A and the active ingredient B applied alone and in combination were shown in the tables, and a total 15 groups were designed. Water containing the solvent and emulsifier same with the above groups but free of the agents was used as a blank control.

2.2.2) Repetition of Experiments 3 pots with 20 weed seeds per pot were treated in one treatment with 4 replications per treatment, that is, a total of 60 weeds were treated in one treatment.

2.3) Treatment Method 2.3.1) The Timing and Frequency of the Treatment

The agents were used for only once in the experiment. In the stage of weeds with 2 leaves and 1 core, the weeds were thinned out to maintain 15 weeds per pot and 45 weeds for each treatment, then continued to be cultured to 3-5-leaves stage of *Capsella bursa-pastoris* and *Myosoton aquaticum*, and 3-leaves and 1-core stage of *Alopecurus japonicus*, and treated.

2.3.2) Equipments and Methods for Applying Agents

The well-cultured weeds were evenly placed on a platform with an area of 0.5 m$^2$, and a solution of agents was sprayed on the stems and leaves thereof by the 3WP-2000-type walking spray tower at a dosage of 30 kg/ha and at a spray pressure of 0.3 MPa. After all the solution was sprayed, the valve was closed. After 30 seconds, the door of the spray tower was opened, and the nutritional bowl was taken out. Then the valve was opened, and the spray tube was cleaned by spraying 50 ml of water.

3) Experimental Methods

A pot-culture method was employed. For the cultivation of weeds, please refer to the Section 1.2, and "Pesticide guidelines for laboratory bioactivity tests—herbicides". As to a method for applying agents, please refer to the section 2.3.2, that is, a method for treating stems and leaves was employed.

4) Data Investigation and Statistical Analysis 4.1) Investigation Methods

A method for investigating absolute number was employed, wherein whole seedlings of survival weeds were cut off with a blade along the soil surface, and the fresh weight of the weeds was weighed with an analytical balance. For dead weeds, the fresh weight thereof was zero.

4.2) Investigation Timing and Frequency

The investigation was performed after 20 days of the treatment for only once.

4.3) Statistical Analysis of the Data

Theoretical fresh weight inhibition rate of a combination of two active ingredients in each group was calculated by the Gowing method ($E0=X+Y-X*Y/100$), and then compared with an actually measured inhibition rate (E), thereby effect of the combination (hereafter referred to as combined effect) on weeds was evaluated: the value of E-E0, which was greater than 10%, corresponded to a synergistic effect, the value of E-E0, which was less than −10%, corresponded to an antagonistic effect, and the value of E-E0, which was from −10% to 10%, corresponded to an additional effect. An optimum ratio of the two active ingredients was determined by the actual control effect, characteristics of herbicides, and balance of a corresponding formula.

Wherein, in the formula, X represented the fresh weight inhibition rate of the active ingredient A in a dosage of P, and Y represented the fresh weight inhibition rate of the active ingredient B in a dosage of Q.

The statistical results were shown in the tables below.

TABLE 1

Actual control effect and combined effect of a combination of the active ingredient A and MCPA on weeds (Gowing method)

| Agents | dosage of active ingredient (g/hm$^2$) | *Capsella bursa-pastoris* | | | *Myosoton aquaticum* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| MCPA | 300 | 33.2 | — | — | 23.8 | — | — |
| | 600 | 41.7 | — | — | 35.6 | — | — |
| | 900 | 60.5 | — | — | 45.8 | — | — |

TABLE 1-continued

Actual control effect and combined effect of a combination of
the active ingredient A and MCPA on weeds (Gowing method)

| Agents | dosage of active ingredient (g/hm²) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A + MCPA | 15 + 300 | 95.4 | 81.5 | 13.9 | 98.2 | 75.2 | 23.0 |
| | 15 + 600 | 97.4 | 83.9 | 13.5 | 100 | 79.0 | 21.0 |
| | 15 + 900 | 100 | 89.1 | 10.9 | 100 | 82.3 | 17.7 |
| | 30 + 300 | 100 | 93.7 | 6.3 | 100 | 90.6 | 9.4 |
| | 30 + 600 | 100 | 94.5 | 5.5 | 100 | 92.0 | 8.0 |
| | 30 + 900 | 100 | 96.2 | 3.8 | 100 | 93.3 | 6.7 |
| | 45 + 300 | 100 | 100.0 | 0.0 | 100 | 100.0 | 0.0 |
| | 45 + 600 | 100 | 100.0 | 0.0 | 100 | 100.0 | 0.0 |
| | 45 + 900 | 100 | 100.0 | 0.0 | 100 | 100.0 | 0.0 |

TABLE 2

Actual control effect and combined effect of a combination of
the active ingredient A and MCPA-Na on weeds (Gowing method)

| agents | dosage of active ingredient (g/hm²) | Capsella bursa-pastoris | | | Myosoton aquaticum | | |
|---|---|---|---|---|---|---|---|
| | | actual fresh weight inhibition rate (%) | theoretical fresh weight inhibition rate (%) | E−E0 | actual fresh weight inhibition rate (%) | theoretical fresh weight inhibition rate (%) | E−E0 |
| active ingredient A | 15 | 72.3 | — | — | 67.4 | — | — |
| | 30 | 90.5 | — | — | 87.6 | — | — |
| | 45 | 100 | — | — | 100 | — | — |
| MCPA-Na | 400 | 22.1 | — | — | 24.8 | — | — |
| | 800 | 38.3 | — | — | 36.9 | — | — |
| | 1200 | 56.7 | — | — | 50.9 | — | — |
| active ingredient A + MCPA-Na | 15 + 400 | 97.4 | 78.4 | 19.0 | 98.2 | 75.5 | 22.7 |
| | 15 + 800 | 100 | 82.9 | 17.1 | 100 | 79.4 | 20.6 |
| | 15 + 1200 | 100 | 88.0 | 12.0 | 100 | 84.0 | 16.0 |
| | 30 + 400 | 100 | 92.6 | 7.4 | 100 | 90.7 | 9.3 |
| | 30 + 800 | 100 | 94.1 | 5.9 | 100 | 92.2 | 7.8 |
| | 30 + 1200 | 100 | 95.9 | 4.1 | 100 | 93.9 | 6.1 |
| | 45 + 400 | 100 | 100.0 | 0.0 | 100 | 100.0 | 0.0 |
| | 45 + 800 | 100 | 100.0 | 0.0 | 100 | 100.0 | 0.0 |
| | 45 + 1200 | 100 | 100.0 | 0.0 | 100 | 100.0 | 0.0 |

TABLE 3

Actual control effect and combined effect of a combination of the active
ingredient A and MCPA-isooctyl on weeds (Gowing method)

| agents | dosage of active ingredient (g/hm²) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| MCPA-isooctyl | 600 | 33.2 | — | — | 23.8 | — | — |
| | 1200 | 41.7 | — | — | 35.6 | — | — |
| | 1800 | 60.5 | — | — | 45.8 | — | — |
| active ingredient A + MCPA-isooctyl | 15 + 600 | 95.4 | 81.5 | 13.9 | 91.4 | 75.2 | 16.2 |
| | 15 + 1200 | 100 | 83.9 | 16.1 | 95.6 | 79.0 | 16.6 |
| | 15 + 1800 | 100 | 89.1 | 10.9 | 98.7 | 82.3 | 16.4 |
| | 30 + 600 | 100 | 93.7 | 6.3 | 100 | 90.6 | 9.4 |
| | 30 + 1200 | 100 | 94.5 | 5.5 | 100 | 92.0 | 8.0 |
| | 30 + 1800 | 100 | 96.2 | 3.8 | 100 | 93.3 | 6.7 |

TABLE 3-continued

Actual control effect and combined effect of a combination of the active ingredient A and MCPA-isooctyl on weeds (Gowing method)

| | | Capsella bursa-pastoris | | | Myosoton aquaticum | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| | 45 + 600 | 100 | 100.0 | 0.0 | 100 | 100.0 | 0.0 |
| | 45 + 1200 | 100 | 100.0 | 0.0 | 100 | 100.0 | 0.0 |
| | 45 + 1800 | 100 | 100.0 | 0.0 | 100 | 100.0 | 0.0 |

TABLE 4

Actual control effect and combined effect of a combination of the active ingredient A and MCPA-dimethylammonium on weeds (Gowing method)

| | | Capsella bursa-pastoris | | | Myosoton aquaticum | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| MCPA-dimethylammonium | 550 | 29.2 | — | — | 26.7 | — | — |
| | 950 | 43.6 | — | — | 33.1 | — | — |
| | 1350 | 59.2 | — | — | 47.2 | — | — |
| active ingredient A + MCPA-dimethylammonium | 15 + 550 | 95.4 | 80.4 | 15.0 | 98.2 | 76.1 | 22.1 |
| | 15 + 950 | 100 | 84.4 | 15.6 | 100 | 78.2 | 21.8 |
| | 15 + 1350 | 100 | 88.7 | 11.3 | 100 | 82.8 | 17.2 |
| | 30 + 550 | 100 | 93.3 | 6.7 | 100 | 90.9 | 9.1 |
| | 30 + 950 | 100 | 94.6 | 5.4 | 100 | 91.7 | 8.3 |
| | 30 + 1350 | 100 | 96.1 | 3.9 | 100 | 93.5 | 6.5 |
| | 45 + 550 | 100 | 100.0 | 0.0 | 100 | 100.0 | 0.0 |
| | 45 + 950 | 100 | 100.0 | 0.0 | 100 | 100.0 | 0.0 |
| | 45 + 1350 | 100 | 100.0 | 0.0 | 100 | 100.0 | 0.0 |

TABLE 5

Actual control effect and combined effect of a combination of the active ingredient A and 2,4-butyl este on weeds (Gowing method)

| | | Capsella bursa-pastoris | | | Myosoton aquaticum | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| 2,4-butyl ester | 200 | 23.4 | — | — | 18.4 | — | — |
| | 350 | 42.9 | — | — | 29.8 | — | — |
| | 500 | 55.6 | — | — | 49.3 | — | — |
| active ingredient A + 2,4-butyl ester | 15 + 200 | 91.8 | 78.8 | 13.0 | 89.8 | 73.4 | 16.4 |
| | 15 + 350 | 99.2 | 84.2 | 15.0 | 96.2 | 77.1 | 19.1 |
| | 15 + 500 | 100 | 87.7 | 12.3 | 100 | 83.5 | 16.5 |
| | 30 + 200 | 100 | 92.7 | 7.3 | 100 | 89.9 | 10.1 |
| | 30 + 350 | 100 | 94.6 | 5.4 | 100 | 91.3 | 8.7 |
| | 30 + 500 | 100 | 95.8 | 4.2 | 100 | 93.7 | 6.3 |
| | 45 + 200 | 100 | 100.0 | 0.0 | 100 | 100.0 | 0.0 |
| | 45 + 350 | 100 | 100.0 | 0.0 | 100 | 100.0 | 0.0 |
| | 45 + 500 | 100 | 100.0 | 0.0 | 100 | 100.0 | 0.0 |

TABLE 6

Actual control effect and combined effect of a combination of the active ingredient A and 2,4-D isooctyl ester on weeds (Gowing method)

| agents | dosage of active ingredient (g/hm²) | *Capsella bursa-pastoris* | | | *Myosoton aquaticum* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| 2,4-D isooctyl ester | 200 | 21.1 | — | — | 15.4 | — | — |
| | 350 | 34.2 | — | — | 26.3 | — | — |
| | 500 | 55.9 | — | — | 47.9 | — | — |
| active ingredient A + 2,4-D isooctyl ester | 15 + 200 | 92.5 | 78.1 | 14.4 | 87.9 | 72.4 | 15.5 |
| | 15 + 350 | 97.8 | 81.8 | 16.0 | 91.2 | 76.0 | 15.2 |
| | 15 + 500 | 100 | 87.8 | 12.2 | 100 | 83.0 | 17.0 |
| | 30 + 200 | 100 | 92.5 | 7.5 | 100 | 89.5 | 10.5 |
| | 30 + 350 | 100 | 93.7 | 6.3 | 100 | 90.9 | 9.1 |
| | 30 + 500 | 100 | 95.8 | 4.2 | 100 | 93.5 | 6.5 |
| | 45 + 200 | 100 | 100.0 | 0.0 | 100 | 100.0 | 0.0 |
| | 45 + 350 | 100 | 100.0 | 0.0 | 100 | 100.0 | 0.0 |
| | 45 + 500 | 100 | 100.0 | 0.0 | 100 | 100.0 | 0.0 |

TABLE 7

Actual control effect and combined effect of a combination of the active ingredient A and fluroxypyr on weeds (Gowing method)

| Agents | dosage of active ingredient (g/hm²) | *Capsella bursa-pastoris* | | | *Myosoton aquaticum* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| fluroxypyr | 100 | 10.1 | — | — | 90.1 | — | — |
| | 150 | 18.3 | — | — | 100 | — | — |
| | 200 | 28.7 | — | — | 100 | — | — |
| active ingredient A + fluroxypyr | 15 + 100 | 91.8 | 75.1 | 16.7 | 97.6 | 96.8 | 0.8 |
| | 15 + 150 | 95.8 | 77.4 | 18.4 | 100 | 100.0 | 0.0 |
| | 15 + 200 | 100 | 80.2 | 19.8 | 100 | 100.0 | 0.0 |
| | 30 + 100 | 100 | 91.5 | 8.5 | 100 | 98.8 | 1.2 |
| | 30 + 150 | 100 | 92.2 | 7.8 | 100 | 100.0 | 0.0 |
| | 30 + 200 | 100 | 93.2 | 6.8 | 100 | 100.0 | 0.0 |
| | 45 + 100 | 100 | 100.0 | 0.0 | 100 | 100.0 | 0.0 |
| | 45 + 150 | 100 | 100.0 | 0.0 | 100 | 100.0 | 0.0 |
| | 45 + 200 | 100 | 100.0 | 0.0 | 100 | 100.0 | 0.0 |

TABLE 8

Actual control effect and combined effect of a combination of the active ingredient A and halauxifen-methyl on weeds (Gowing method)

| agents | dosage of active ingredient (g/hm²) | *Capsella bursa-pastoris* | | | *Myosoton aquaticum* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| halauxifen-methyl | 5 | 59.7 | — | — | 17.5 | — | — |
| | 7.5 | 62.5 | — | — | 27.8 | — | — |
| | 10 | 71.4 | — | — | 35.6 | — | — |

TABLE 8-continued

Actual control effect and combined effect of a combination of the active ingredient A and halauxifen-methyl on weeds (Gowing method)

| agents | dosage of active ingredient (g/hm$^2$) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A + halauxifen-methyl | 15 + 5 | 100 | 88.8 | 11.2 | 97.6 | 73.1 | 24.5 |
| | 15 + 7.5 | 100 | 89.6 | 10.4 | 100 | 76.5 | 23.5 |
| | 15 + 10 | 100 | 92.1 | 7.9 | 100 | 79.0 | 21.0 |
| | 30 + 5 | 100 | 96.2 | 3.8 | 100 | 89.8 | 10.2 |
| | 30 + 7.5 | 100 | 96.4 | 3.6 | 100 | 91.0 | 9.0 |
| | 30 + 10 | 100 | 97.3 | 2.7 | 100 | 92.0 | 8.0 |
| | 45 + 5 | 100 | 100.0 | 0.0 | 100 | 100.0 | 0.0 |
| | 45 + 7.5 | 100 | 100.0 | 0.0 | 100 | 100.0 | 0.0 |
| | 45 + 10 | 100 | 100.0 | 0.0 | 100 | 100.0 | 0.0 |

TABLE 9

Actual control effect and combined effect of a combination of the active ingredient A and carfentrazone on weeds (Gowing method)

| agents | dosage of active ingredient (g/hm$^2$) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| carfentrazone | 12 | 55.2 | — | — | 32.1 | — | — |
| | 24 | 71.3 | — | — | 45.8 | — | — |
| | 36 | 80.5 | — | — | 60.1 | — | — |
| active ingredient A + carfentrazone | 15 + 12 | 100 | 87.6 | 12.4 | 89.2 | 77.9 | 11.3 |
| | 15 + 24 | 100 | 92.1 | 7.9 | 98.4 | 82.3 | 16.1 |
| | 15 + 36 | 100 | 94.6 | 5.4 | 100 | 87.0 | 13.0 |
| | 30 + 12 | 100 | 95.7 | 4.3 | 100 | 91.6 | 8.4 |
| | 30 + 24 | 100 | 97.3 | 2.7 | 100 | 93.3 | 6.7 |
| | 30 + 36 | 100 | 98.1 | 1.9 | 100 | 95.1 | 4.9 |
| | 45 + 12 | 100 | 100.0 | 0.0 | 100 | 100.0 | 0.0 |
| | 45 + 24 | 100 | 100.0 | 0.0 | 100 | 100.0 | 0.0 |
| | 45 + 36 | 100 | 100.0 | 0.0 | 100 | 100.0 | 0.0 |

TABLE 10

Actual control effect and combined effect of a combination of the active ingredient A and fluoroglycofen on weeds (Gowing method)

| agents | dosage of active ingredient (g/hm$^2$) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| fluoroglycofen | 5 | 47.4 | — | — | 37.9 | — | — |
| | 10 | 61.6 | — | — | 41.8 | — | — |
| | 15 | 70.5 | — | — | 55.4 | — | — |
| active ingredient A + fluoroglycofen | 15 + 5 | 100 | 85.4 | 14.6 | 94.7 | 79.8 | 14.9 |
| | 15 + 10 | 100 | 89.4 | 10.6 | 98.2 | 81.0 | 17.2 |
| | 15 + 15 | 100 | 91.8 | 8.2 | 100 | 85.5 | 14.5 |
| | 30 + 5 | 100 | 95.0 | 5.0 | 100 | 92.3 | 7.7 |
| | 30 + 10 | 100 | 96.4 | 3.6 | 100 | 92.8 | 7.2 |
| | 30 + 15 | 100 | 97.2 | 2.8 | 100 | 94.5 | 5.5 |

TABLE 10-continued

Actual control effect and combined effect of a combination of the active ingredient A and fluoroglycofen on weeds (Gowing method)

| | | *Capsella bursa-pastoris* | | | *Myosoton aquaticum* | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| | 45 + 5 | 100 | 100.0 | 0.0 | 100 | 100.0 | 0.0 |
| | 45 + 10 | 100 | 100.0 | 0.0 | 100 | 100.0 | 0.0 |
| | 45 + 15 | 100 | 100.0 | 0.0 | 100 | 100.0 | 0.0 |

TABLE 11

Actual control effect and combined effect of a combination of the active ingredient A and metribuzin on weeds (Gowing method)

| | | *Capsella bursa-pastoris* | | | *Myosoton aquaticum* | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| metribuzin | 13.5 | 55.6 | — | — | 42.1 | — | — |
| | 25 | 64.1 | — | — | 52.9 | — | — |
| | 36.5 | 82.3 | — | — | 58.5 | — | — |
| active ingredient A + metribuzin | 15 + 13.5 | 100 | 87.7 | 12.3 | 92.1 | 81.1 | 11.0 |
| | 15 + 25 | 100 | 90.1 | 9.9 | 95.5 | 84.6 | 10.9 |
| | 15 + 36.5 | 100 | 95.1 | 4.9 | 97.7 | 86.5 | 11.2 |
| | 30 + 13.5 | 100 | 95.8 | 4.2 | 100 | 92.8 | 7.2 |
| | 30 + 25 | 100 | 96.6 | 3.4 | 100 | 94.2 | 5.8 |
| | 30 + 36.5 | 100 | 98.3 | 1.7 | 100 | 94.9 | 5.1 |
| | 45 + 13.5 | 100 | 100.0 | 0.0 | 100 | 100.0 | 0.0 |
| | 45 + 25 | 100 | 100.0 | 0.0 | 100 | 100.0 | 0.0 |
| | 45 + 36.5 | 100 | 100.0 | 0.0 | 100 | 100.0 | 0.0 |

TABLE 12

Actual control effect and combined effect of a combination of the active ingredient A and prometryn on weeds (Gowing method)

| | | *Capsella bursa-pastoris* | | | *Myosoton aquaticum* | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| prometryn | 150 | 20.4 | — | — | 22.6 | — | — |
| | 450 | 29.6 | — | — | 33.7 | — | — |
| | 750 | 45.7 | — | — | 45.2 | — | — |
| active ingredient A + prometryn | 15 + 150 | 91.2 | 78.0 | 13.2 | 87.3 | 74.8 | 12.5 |
| | 15 + 450 | 98.9 | 80.5 | 18.4 | 91.6 | 78.4 | 13.2 |
| | 15 + 750 | 100 | 85.0 | 15.0 | 98.2 | 82.1 | 16.1 |
| | 30 + 150 | 100 | 92.4 | 7.6 | 100 | 90.4 | 9.6 |
| | 30 + 450 | 100 | 93.3 | 6.7 | 100 | 91.8 | 8.2 |
| | 30 + 750 | 100 | 94.8 | 5.2 | 100 | 93.2 | 6.8 |
| | 45 + 150 | 100 | 100.0 | 0.0 | 100 | 100.0 | 0.0 |
| | 45 + 450 | 100 | 100.0 | 0.0 | 100 | 100.0 | 0.0 |
| | 45 + 750 | 100 | 100.0 | 0.0 | 100 | 100.0 | 0.0 |

TABLE 13

Actual control effect and combined effect of a combination of the active ingredient A and terbutryn on weeds (Gowing method)

| | | Capsella bursa-pastoris | | | Myosoton aquaticum | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| terbutryn | 125 | 15.4 | — | — | 13.4 | — | — |
| | 275 | 25.3 | — | — | 29.3 | — | — |
| | 425 | 40.9 | — | — | 33.9 | — | — |
| active ingredient A + terbutryn | 15 + 125 | 88.6 | 76.6 | 12.0 | 85.7 | 71.8 | 13.9 |
| | 15 + 275 | 92.3 | 79.3 | 13.0 | 89.5 | 77.0 | 12.5 |
| | 15 + 425 | 100 | 83.6 | 16.4 | 91.7 | 78.5 | 13.2 |
| | 30 + 125 | 100 | 92.0 | 8.0 | 100 | 89.3 | 10.7 |
| | 30 + 275 | 100 | 92.9 | 7.1 | 100 | 91.2 | 8.8 |
| | 30 + 425 | 100 | 94.4 | 5.6 | 100 | 91.8 | 8.2 |
| | 45 + 125 | 100 | 100.0 | 0.0 | 100 | 100.0 | 0.0 |
| | 45 + 275 | 100 | 100.0 | 0.0 | 100 | 100.0 | 0.0 |
| | 45 + 425 | 100 | 100.0 | 0.0 | 100 | 100.0 | 0.0 |

TABLE 14

Actual control effect and combined effect of a combination of the active ingredient A and florasulam on weeds (Gowing method)

| | | Capsella bursa-pastoris | | | Myosoton aquaticum | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| florasulam | 2.5 | 45.8 | — | — | 28.3 | — | — |
| | 5 | 60.4 | — | — | 41.9 | — | — |
| | 7.5 | 78.2 | — | — | 55.3 | — | — |
| active ingredient A + florasulam | 15 + 2.5 | 99.3 | 85.0 | 14.3 | 87.2 | 76.6 | 10.6 |
| | 15 + 5 | 100 | 89.0 | 11.0 | 93.4 | 81.1 | 12.3 |
| | 15 + 7.5 | 100 | 94.0 | 6.0 | 99.6 | 85.4 | 14.2 |
| | 30 + 2.5 | 100 | 94.9 | 5.1 | 100 | 91.1 | 8.9 |
| | 30 + 5 | 100 | 96.2 | 3.8 | 100 | 92.8 | 7.2 |
| | 30 + 7.5 | 100 | 97.9 | 2.1 | 100 | 94.5 | 5.5 |
| | 45 + 2.5 | 100 | 100.0 | 0.0 | 100 | 100.0 | 0.0 |
| | 45 + 5 | 100 | 100.0 | 0.0 | 100 | 100.0 | 0.0 |
| | 45 + 7.5 | 100 | 100.0 | 0.0 | 100 | 100.0 | 0.0 |

TABLE 15

Actual control effect and combined effect of a combination of the active ingredient A and bentazon on weeds (Gowing method)

| | | Capsella bursa-pastoris | | | Myosoton aquaticum | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| bentazon | 500 | 38.5 | — | — | 33.4 | — | — |
| | 750 | 58.2 | — | — | 46.2 | — | — |
| | 1000 | 73.1 | — | — | 58.7 | — | — |

TABLE 15-continued

Actual control effect and combined effect of a combination of the active
ingredient A and bentazon on weeds (Gowing method)

| | | Capsella bursa-pastoris | | | Myosoton aquaticum | | |
|---|---|---|---|---|---|---|---|
| agents | dosage of active ingredient (g/hm²) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A + bentazon | 15 + 500 | 96.4 | 83.0 | 13.4 | 90.2 | 78.3 | 11.9 |
| | 15 + 750 | 100 | 88.4 | 11.6 | 93.5 | 82.5 | 11.0 |
| | 15 + 1000 | 100 | 92.5 | 7.5 | 97.2 | 86.5 | 10.7 |
| | 30 + 500 | 100 | 94.2 | 5.8 | 100 | 91.7 | 8.3 |
| | 30 + 750 | 100 | 96.0 | 4.0 | 100 | 93.3 | 6.7 |
| | 30 + 1000 | 100 | 97.4 | 2.6 | 100 | 94.9 | 5.1 |
| | 45 + 500 | 100 | 100.0 | 0.0 | 100 | 100.0 | 0.0 |
| | 45 + 750 | 100 | 100.0 | 0.0 | 100 | 100.0 | 0.0 |
| | 45 + 1000 | 100 | 100.0 | 0.0 | 100 | 100.0 | 0.0 |

TABLE 16

Actual control effect and combined effect of a combination of the active
ingredient A and isoproturon on weeds (Gowing method)

| | | Capsella bursa-pastoris | | | Myosoton aquaticum | | |
|---|---|---|---|---|---|---|---|
| agents | dosage of active ingredient (g/hm²) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| isoproturon | 300 | 21.7 | — | — | 19.4 | — | — |
| | 750 | 33.7 | — | — | 26.4 | — | — |
| | 1200 | 57.2 | — | — | 47.5 | — | — |
| active ingredient A + isoproturon | 15 + 300 | 89.3 | 78.3 | 11.0 | 87.3 | 73.7 | 13.6 |
| | 15 + 750 | 92.1 | 81.6 | 10.5 | 89.5 | 76.0 | 13.5 |
| | 15 + 1200 | 98.3 | 88.1 | 10.2 | 95.7 | 82.9 | 12.8 |
| | 30 + 300 | 100 | 92.6 | 7.4 | 100 | 90.0 | 10.0 |
| | 30 + 750 | 100 | 93.7 | 6.3 | 100 | 90.9 | 9.1 |
| | 30 + 1200 | 100 | 95.9 | 4.1 | 100 | 93.5 | 6.5 |
| | 45 + 300 | 100 | 100.0 | 0.0 | 100 | 100.0 | 0.0 |
| | 45 + 750 | 100 | 100.0 | 0.0 | 100 | 100.0 | 0.0 |
| | 45 + 1200 | 100 | 100.0 | 0.0 | 100 | 100.0 | 0.0 |

TABLE 17

Actual control effect and combined effect of a combination of the active
ingredient A and diflufenican on weeds (Gowing method)

| | | Capsella bursa-pastoris | | | Myosoton aquaticum | | |
|---|---|---|---|---|---|---|---|
| agents | dosage of active ingredient (g/hm²) | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| diflufenican | 40 | 33.1 | — | — | 24.1 | — | — |
| | 80 | 48.2 | — | — | 46.2 | — | — |
| | 120 | 63.4 | — | — | 66.5 | — | — |
| active ingredient A + diflufenican | 15 + 40 | 93.4 | 81.5 | 11.9 | 88.2 | 75.3 | 12.9 |
| | 15 + 80 | 96.7 | 85.7 | 11.0 | 93.4 | 82.5 | 10.9 |
| | 15 + 120 | 100 | 89.9 | 10.1 | 99.7 | 89.1 | 10.6 |
| | 30 + 40 | 100 | 93.6 | 6.4 | 100 | 90.6 | 9.4 |
| | 30 + 80 | 100 | 95.1 | 4.9 | 100 | 93.3 | 6.7 |
| | 30 + 120 | 100 | 96.5 | 3.5 | 100 | 95.8 | 4.2 |

TABLE 17-continued

Actual control effect and combined effect of a combination of the active ingredient A and diflufenican on weeds (Gowing method)

| agents | dosage of active ingredient (g/hm$^2$) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| | 45 + 40 | 100 | 100.0 | 0.0 | 100 | 100.0 | 0.0 |
| | 45 + 80 | 100 | 100.0 | 0.0 | 100 | 100.0 | 0.0 |
| | 45 + 120 | 100 | 100.0 | 0.0 | 100 | 100.0 | 0.0 |

TABLE 18

Actual control effect and combined effect of a combination of the active ingredient A and picolinafen on weeds (Gowing method)

| agents | dosage of active ingredient (g/hm$^2$) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| picolinafen | 40 | 16.4 | — | — | 14.5 | — | — |
| | 80 | 33.2 | — | — | 34.9 | — | — |
| | 120 | 55.6 | — | — | 50.5 | — | — |
| active ingredient A + picolinafen | 15 + 40 | 89.3 | 76.8 | 12.5 | 89.4 | 72.1 | 17.3 |
| | 15 + 80 | 94.5 | 81.5 | 13.0 | 93.1 | 78.8 | 14.3 |
| | 15 + 120 | 100 | 87.7 | 12.3 | 96.3 | 83.9 | 12.4 |
| | 30 + 40 | 100 | 92.1 | 7.9 | 100 | 89.4 | 10.6 |
| | 30 + 80 | 100 | 93.7 | 6.3 | 100 | 91.9 | 8.1 |
| | 30 + 120 | 100 | 95.8 | 4.2 | 100 | 93.9 | 6.1 |
| | 45 + 40 | 100 | 100.0 | 0.0 | 100 | 100.0 | 0.0 |
| | 45 + 80 | 100 | 100.0 | 0.0 | 100 | 100.0 | 0.0 |
| | 45 + 120 | 100 | 100.0 | 0.0 | 100 | 100.0 | 0.0 |

TABLE 19

Actual control effect and combined effect of a combination of the active ingredient A and fenothiocarb on weeds (Gowing method)

| agents | dosage of active ingredient (g/hm$^2$) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 13.2 | — | — |
| | 30 | 90.5 | — | — | 16.5 | — | — |
| | 45 | 100 | — | — | 24.6 | — | — |
| fenothiocarb | 40 | 0 | — | — | 70.3 | — | — |
| | 65 | 0 | — | — | 84.5 | — | — |
| | 90 | 0 | — | — | 97.3 | — | — |
| active ingredient A + fenothiocarb | 15 + 40 | 71.9 | 72.3 | −0.4 | 85.1 | 74.2 | 10.9 |
| | 15 + 65 | 74.1 | 72.3 | 1.8 | 97.2 | 86.5 | 10.7 |
| | 15 + 90 | 74.6 | 72.3 | 2.3 | 100 | 97.7 | 2.3 |
| | 30 + 40 | 91.2 | 90.5 | 0.7 | 100 | 75.2 | 24.8 |
| | 30 + 65 | 90.9 | 90.5 | 0.4 | 100 | 87.1 | 12.9 |
| | 30 + 90 | 91.4 | 90.5 | 0.9 | 100 | 97.7 | 2.3 |
| | 45 + 40 | 100 | 100.0 | 0.0 | 100 | 77.6 | 22.4 |
| | 45 + 65 | 100 | 100.0 | 0.0 | 100 | 88.3 | 11.7 |
| | 45 + 90 | 100 | 100.0 | 0.0 | 100 | 98.0 | 2.0 |

TABLE 20

Actual control effect and combined effect of a combination of
the active ingredient A and clodinafop on weeds (Gowing method)

| agents | dosage of active ingredient (g/hm$^2$) | Capsella bursa-pastoris | | | Alopecurus japonicus | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 13.2 | — | — |
| | 30 | 90.5 | — | — | 16.5 | — | — |
| | 45 | 100 | — | — | 24.6 | — | — |
| clodinafop | 40 | 0 | — | — | 81.3 | — | — |
| | 65 | 0 | — | — | 87.4 | — | — |
| | 90 | 0 | — | — | 95.6 | — | — |
| active ingredient A + clodinafop | 15 + 40 | 72.5 | 72.3 | 0.2 | 94.8 | 83.8 | 11.0 |
| | 15 + 65 | 71.9 | 72.3 | −0.4 | 97.6 | 89.1 | 8.5 |
| | 15 + 90 | 73.2 | 72.3 | 0.9 | 100 | 96.2 | 3.8 |
| | 30 + 40 | 89.9 | 90.5 | −0.6 | 100 | 84.4 | 15.6 |
| | 30 + 65 | 90.2 | 90.5 | −0.3 | 100 | 89.5 | 10.5 |
| | 30 + 90 | 91.5 | 90.5 | 1.0 | 100 | 96.3 | 3.7 |
| | 45 + 40 | 100 | 100.0 | 0.0 | 100 | 85.9 | 14.1 |
| | 45 + 65 | 100 | 100.0 | 0.0 | 100 | 90.5 | 9.5 |
| | 45 + 90 | 100 | 100.0 | 0.0 | 100 | 96.7 | 3.3 |

TABLE 21

Actual control effect and combined effect of a combination of
the active ingredient A and tralkoxydim on weeds (Gowing method)

| agents | dosage of active ingredient (g/hm$^2$) | Capsella bursa-pastoris | | | Alopecurus japonicus | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 13.2 | — | — |
| | 30 | 90.5 | — | — | 16.5 | — | — |
| | 45 | 100 | — | — | 24.6 | — | — |
| tralkoxydim | 240 | 0 | — | — | 74.5 | — | — |
| | 360 | 0 | — | — | 81.2 | — | — |
| | 480 | 0 | — | — | 89.8 | — | — |
| active ingredient A + tralkoxydim | 15 + 240 | 72.5 | 72.3 | 0.2 | 88.2 | 77.9 | 10.3 |
| | 15 + 360 | 71.8 | 72.3 | −0.5 | 93.9 | 83.7 | 10.2 |
| | 15 + 480 | 73.4 | 72.3 | 1.1 | 100 | 91.1 | 8.9 |
| | 30 + 240 | 89.6 | 90.5 | −0.9 | 100 | 78.7 | 21.3 |
| | 30 + 360 | 91.3 | 90.5 | 0.8 | 100 | 84.3 | 15.7 |
| | 30 + 480 | 91.7 | 90.5 | 1.2 | 100 | 91.5 | 8.5 |
| | 45 + 240 | 100 | 100.0 | 0.0 | 100 | 80.8 | 19.2 |
| | 45 + 360 | 100 | 100.0 | 0.0 | 100 | 85.8 | 14.2 |
| | 45 + 480 | 100 | 100.0 | 0.0 | 100 | 92.3 | 7.7 |

TABLE 22

Actual control effect and combined effect of a combination of the active
ingredient A and halosulfuron-methyl on weeds (Gowing method)

| agents | dosage of active ingredient (g/hm$^2$) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| halosulfuron-methyl | 30 | 17.9 | — | — | 14.5 | — | — |
| | 50 | 27.8 | — | — | 34.9 | — | — |
| | 70 | 44.1 | — | — | 50.5 | — | — |

TABLE 22-continued

Actual control effect and combined effect of a combination of the active ingredient A and halosulfuron-methyl on weeds (Gowing method)

| agents | dosage of active ingredient (g/hm²) | *Capsella bursa-pastoris* | | | *Myosoton aquaticum* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A + halosulfuron-methyl | 15 + 30 | 89.2 | 77.3 | 11.9 | 84.1 | 72.1 | 12.0 |
| | 15 + 50 | 91.4 | 80.0 | 11.4 | 90.2 | 78.8 | 11.4 |
| | 15 + 70 | 95.6 | 84.5 | 11.1 | 94.9 | 83.9 | 11.0 |
| | 30 + 30 | 100 | 92.2 | 7.8 | 100 | 89.4 | 10.6 |
| | 30 + 50 | 100 | 93.1 | 6.9 | 100 | 91.9 | 8.1 |
| | 30 + 70 | 100 | 94.7 | 5.3 | 100 | 93.9 | 6.1 |
| | 45 + 30 | 100 | 100.0 | 0.0 | 100 | 100.0 | 0.0 |
| | 45 + 50 | 100 | 100.0 | 0.0 | 100 | 100.0 | 0.0 |
| | 45 + 70 | 100 | 100.0 | 0.0 | 100 | 100.0 | 0.0 |

TABLE 23

Actual control effect and combined effect of a combination of the active ingredient A and mesosulfuron-methyl on weeds (Gowing method)

| agents | dosage of active ingredient (g/hm²) | *Capsella bursa-pastoris* | | | *Alopecurus japonicus* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 13.2 | — | — |
| | 30 | 90.5 | — | — | 16.5 | — | — |
| | 45 | 100 | — | — | 24.6 | — | — |
| mesosulfuron-methyl | 6 | 24.5 | — | — | 67.9 | — | — |
| | 9 | 37.6 | — | — | 73.2 | — | — |
| | 12 | 63.4 | — | — | 88.9 | — | — |
| active ingredient A + mesosulfuron-methyl | 15 + 6 | 90.1 | 79.1 | 11.0 | 87.2 | 72.1 | 15.1 |
| | 15 + 9 | 93.4 | 82.7 | 10.7 | 90.9 | 76.7 | 14.2 |
| | 15 + 12 | 100 | 89.9 | 10.1 | 97.6 | 90.4 | 7.2 |
| | 30 + 6 | 100 | 92.8 | 7.2 | 89.7 | 73.2 | 16.5 |
| | 30 + 9 | 100 | 94.1 | 5.9 | 93.3 | 77.6 | 15.7 |
| | 30 + 12 | 100 | 96.5 | 3.5 | 100 | 90.7 | 9.3 |
| | 45 + 6 | 100 | 100.0 | 0.0 | 100 | 75.8 | 24.2 |
| | 45 + 9 | 100 | 100.0 | 0.0 | 100 | 79.8 | 20.2 |
| | 45 + 12 | 100 | 100.0 | 0.0 | 100 | 91.6 | 8.4 |

TABLE 24

Actual control effect and combined effect of a combination of the active ingredient A and flucarbazone-sodium on weeds (Gowing method)

| agents | dosage of active ingredient (g/hm²) | *Capsella bursa-pastoris* | | | *Alopecurus japonicus* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 13.2 | — | — |
| | 30 | 90.5 | — | — | 16.5 | — | — |
| | 45 | 100 | — | — | 24.6 | — | — |
| Flucarbazone-sodium | 20 | 25.6 | — | — | 69.6 | — | — |
| | 35 | 42.7 | — | — | 80.3 | — | — |
| | 50 | 65.1 | — | — | 85.6 | — | — |
| active ingredient A + flucarbazone-sodium | 15 + 20 | 90.1 | 79.4 | 10.7 | 84.9 | 73.6 | 11.3 |
| | 15 + 35 | 94.3 | 84.1 | 10.2 | 94.1 | 82.9 | 11.2 |
| | 15 + 50 | 100 | 90.3 | 9.7 | 98.2 | 87.5 | 10.7 |
| | 30 + 20 | 100 | 92.9 | 7.1 | 85.7 | 74.6 | 11.1 |
| | 30 + 35 | 100 | 94.6 | 5.4 | 94.9 | 83.6 | 11.3 |
| | 30 + 50 | 100 | 96.7 | 3.3 | 97.8 | 88.0 | 9.8 |

TABLE 24-continued

Actual control effect and combined effect of a combination of the active ingredient A and flucarbazone-sodium on weeds (Gowing method)

| | | Capsella bursa-pastoris | | | Alopecurus japonicus | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| | 45 + 20 | 100 | 100.0 | 0.0 | 100 | 77.1 | 22.9 |
| | 45 + 35 | 100 | 100.0 | 0.0 | 100 | 85.1 | 14.9 |
| | 45 + 50 | 100 | 100.0 | 0.0 | 100 | 89.1 | 10.9 |

TABLE 25

Actual control effect and combined effect of a combination of the active ingredient A and pyroxsulam on weeds (Gowing method)

| | | Capsella bursa-pastoris | | | Alopecurus japonicus | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active | 15 | 72.3 | — | — | 13.2 | — | — |
| ingredient | 30 | 90.5 | — | — | 16.5 | — | — |
| A | 45 | 100 | — | — | 24.6 | — | — |
| pyroxsulam | 5 | 19.4 | — | — | 63.5 | — | — |
| | 10 | 31.7 | — | — | 81.9 | — | — |
| | 15 | 55.6 | — | — | 91.5 | — | — |
| active | 15 + 5 | 90.1 | 77.7 | 12.4 | 79.3 | 68.3 | 11.0 |
| ingredient | 15 + 10 | 92.3 | 81.1 | 11.2 | 95.1 | 84.3 | 10.8 |
| A + | 15 + 15 | 98.2 | 87.7 | 10.5 | 100 | 92.6 | 7.4 |
| pyroxsulam | 30 + 5 | 100 | 92.3 | 7.7 | 80.2 | 69.5 | 10.7 |
| | 30 + 10 | 100 | 93.5 | 6.5 | 96.3 | 84.9 | 11.4 |
| | 30 + 15 | 100 | 95.8 | 4.2 | 100 | 92.9 | 7.1 |
| | 45 + 5 | 100 | 100.0 | 0.0 | 84.4 | 72.5 | 11.9 |
| | 45 + 10 | 100 | 100.0 | 0.0 | 100 | 86.4 | 13.6 |
| | 45 + 15 | 100 | 100.0 | 0.0 | 100 | 93.6 | 6.4 |

TABLE 26

Actual control effect and combined effect of a combination of the active ingredient A and pinoxaden on weeds (Gowing method)

| | | Capsella bursa-pastoris | | | Alopecurus japonicus | | |
|---|---|---|---|---|---|---|---|
| agents | dosage of active ingredient (g/hm$^2$) | actual fresh weight inhibition rate (%) | theoretical fresh weight inhibition rate (%) | E − E0 | actual fresh weight inhibition rate (%) | theoretical fresh weight inhibition rate (%) | E − E0 |
| active | 15 | 72.3 | — | — | 13.2 | — | — |
| ingredient | 30 | 90.5 | — | — | 16.5 | — | — |
| A | 45 | 100 | — | — | 24.6 | — | — |
| pinoxaden | 60 | 0 | — | — | 69.2 | — | — |
| | 80 | 0 | — | — | 78.6 | — | — |
| | 120 | 0 | — | — | 85.2 | — | — |
| active | 15 + 60 | 72.2 | 72.3 | −0.1 | 84.5 | 73.3 | 11.2 |
| ingredient | 15 + 80 | 72.8 | 72.3 | 0.5 | 92.3 | 81.4 | 10.9 |
| A + | 15 + 120 | 73.2 | 72.3 | 0.9 | 97.9 | 87.2 | 10.7 |
| pinoxaden | 30 + 60 | 90.2 | 90.5 | −0.3 | 84.9 | 74.3 | 10.6 |
| | 30 + 80 | 91.2 | 90.5 | 0.7 | 92.5 | 82.1 | 10.4 |
| | 30 + 120 | 90.7 | 90.5 | 0.2 | 97.8 | 87.6 | 10.2 |
| | 45 + 60 | 100 | 100.0 | 0.0 | 89.4 | 76.8 | 12.6 |
| | 45 + 80 | 100 | 100.0 | 0.0 | 95.6 | 83.9 | 11.7 |
| | 45 + 120 | 100 | 100.0 | 0.0 | 100 | 88.8 | 11.2 |

TABLE 27

Actual control effect and combined effect of a combination of
the active ingredient A and bromoxynil on weeds (Gowing method)

| Agents | dosage of active ingredient (g/hm²) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| Active ingredient A | 15 | 72.3 | — | — | 67.4 | — | — |
| | 30 | 90.5 | — | — | 87.6 | — | — |
| | 45 | 100 | — | — | 100 | — | — |
| Bromoxynil | 240 | 40.6 | — | — | 30.5 | — | — |
| | 360 | 58.5 | — | — | 38.7 | — | — |
| | 480 | 81.3 | — | — | 47.9 | — | — |
| Active ingredient A + bromoxynil | 15 + 240 | 94.6 | 83.5 | 11.1 | 88.5 | 77.3 | 11.2 |
| | 15 + 360 | 99.1 | 88.5 | 10.6 | 91.2 | 80.0 | 11.2 |
| | 15 + 480 | 100 | 94.8 | 5.2 | 93.4 | 83.0 | 10.4 |
| | 30 + 240 | 100 | 94.4 | 5.6 | 100 | 91.4 | 8.6 |
| | 30 + 360 | 100 | 96.1 | 3.9 | 100 | 92.4 | 7.6 |
| | 30 + 480 | 100 | 98.2 | 1.8 | 100 | 93.5 | 6.5 |
| | 45 + 240 | 100 | 100.0 | 0.0 | 100 | 100.0 | 0.0 |
| | 45 + 360 | 100 | 100.0 | 0.0 | 100 | 100.0 | 0.0 |
| | 45 + 480 | 100 | 100.0 | 0.0 | 100 | 100.0 | 0.0 |

TABLE 28

Actual control effect and combined effect of a combination of the active
ingredient A and bromoxynil octanoate on weeds (Gowing method)

| agents | dosage of active ingredient (g/hm²) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| bromoxynil octanoate | 190 | 42.7 | — | — | 25.8 | — | — |
| | 375 | 55.7 | — | — | 38.5 | — | — |
| | 560 | 78.6 | — | — | 57.3 | — | — |
| active ingredient A + bromoxynil octanoate | 15 + 190 | 95.8 | 84.1 | 11.7 | 88.1 | 75.8 | 12.3 |
| | 15 + 375 | 99.3 | 87.7 | 11.6 | 91.5 | 80.0 | 11.5 |
| | 15 + 560 | 100 | 94.1 | 5.9 | 97.4 | 86.1 | 11.3 |
| | 30 + 190 | 100 | 94.6 | 5.4 | 100 | 90.8 | 9.2 |
| | 30 + 375 | 100 | 95.8 | 4.2 | 100 | 92.4 | 7.6 |
| | 30 + 560 | 100 | 98.0 | 2.0 | 100 | 94.7 | 5.3 |
| | 45 + 190 | 100 | 100.0 | 0.0 | 100 | 100.0 | 0.0 |
| | 45 + 375 | 100 | 100.0 | 0.0 | 100 | 100.0 | 0.0 |
| | 45 + 560 | 100 | 100.0 | 0.0 | 100 | 100.0 | 0.0 |

TABLE 29

Actual control effect and combined effect of a combination of the
active ingredient A and chlorotoluron on weeds (Gowing method)

| agents | dosage of active ingredient (g/hm²) | Capsella bursa-pastoris | | | Myosoton aquaticum | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A | 15 | 72.3 | — | — | 67.4 | — | — |
| | 30 | 90.5 | — | — | 87.6 | — | — |
| | 45 | 100 | — | — | 100 | — | — |
| chlorotoluron | 1500 | 33.5 | — | — | 34.7 | — | — |
| | 2250 | 43.7 | — | — | 43.8 | — | — |
| | 3000 | 57.3 | — | — | 60.1 | — | — |

TABLE 29-continued

Actual control effect and combined effect of a combination of the
active ingredient A and chlorotoluron on weeds (Gowing method)

| agents | dosage of active ingredient (g/hm²) | *Capsella bursa-pastoris* | | | *Myosoton aquaticum* | | |
|---|---|---|---|---|---|---|---|
| | | actual fresh weight inhibition rate (%) | theoretical fresh weight inhibition rate (%) | E − E0 | actual fresh weight inhibition rate (%) | theoretical fresh weight inhibition rate (%) | E − E0 |
| active ingredient A + chlorotoluron | 15 + 1500 | 95.8 | 81.6 | 14.2 | 90.1 | 78.7 | 11.4 |
| | 15 + 2250 | 97.3 | 84.4 | 12.9 | 93.3 | 81.7 | 11.6 |
| | 15 + 3000 | 100 | 88.2 | 11.8 | 97.4 | 87.0 | 10.4 |
| | 30 + 1500 | 100 | 93.7 | 6.3 | 100 | 91.9 | 8.1 |
| | 30 + 2250 | 100 | 94.7 | 5.3 | 100 | 93.0 | 7.0 |
| | 30 + 3000 | 100 | 95.9 | 4.1 | 100 | 95.1 | 4.9 |
| | 45 + 1500 | 100 | 100.0 | 0.0 | 100 | 100.0 | 0.0 |
| | 45 + 2250 | 100 | 100.0 | 0.0 | 100 | 100.0 | 0.0 |
| | 45 + 3000 | 100 | 100.0 | 0.0 | 100 | 100.0 | 0.0 |

1) Experiments on controlling of weeds in wheat fields with the herbicidal compositions prepared in Examples 1.1-7.5

Experimental methods: the weed seeds were all subjected to germination, and the pre-treated weed seeds for the test were evenly spread on the surface of the soil. The weeds were thinned out prior to application of the agents to reach a final singling of 30 weed strains in each pot. 4 pots were employed for each treatment. The agents were sprayed on the stems and leaves of the weeds, the number of dead weeds was investigated, and the control efficiency on weed strains (hereafter referred to weed control efficiency) was calculated (the weed control efficiency in the table was an average value of 4 replicates). The test results were counted after 45 days of the experiment and were shown in Table 30.

$$\text{Weed control efficiency (\%)} = \frac{\text{number of weed strains in water control area} - \text{number of weed strains in area treated with agents}}{\text{number of weed strains in water control area}}$$

TABLE 30

Weed control efficiency of the herbicides of the present invention in wheat fields

| agents | Dosage (g a.i./ha) | Weed control efficiency (%) | | | | safety |
|---|---|---|---|---|---|---|
| | | *Sisymbrium sophia* | *Capsella bursa-pastoris* | *Rorippa indica* (L.) *Hiern* | *Lithospermum arvense* | |
| Example 1.1 (3% emulsifiable concentrate) | 45 | 95.2 | 93.4 | 94.7 | 92.1 | No phytotoxicity |
| | 90 | 100 | 100 | 100 | 100 | No phytotoxicity |
| Example 1.2 (25.5% emulsifiable concentrate) | 382.5 | 94.6 | 92.2 | 93.3 | 92.8 | No phytotoxicity |
| | 765 | 100 | 100 | 100 | 97.7 | No phytotoxicity |
| Example 1.3 (27.5% emulsifiable concentrate) | 412.5 | 94.1 | 93.5 | 94.4 | 96.3 | No phytotoxicity |
| | 825 | 100 | 100 | 100 | 100 | No phytotoxicity |
| Example 1.4 (27.5% emulsifiable concentrate) | 412.5 | 95.6 | 94.7 | 92.9 | 94.5 | No phytotoxicity |
| | 825 | 100 | 100 | 100 | 100 | No phytotoxicity |
| Example 2.1 (17% microemulsion) | 127.5 | 96.2 | 95.7 | 93.8 | 94.1 | No phytotoxicity |
| | 255 | 100 | 100 | 100 | 100 | No phytotoxicity |
| Example 2.2 (8.5% microemulsion) | 127.5 | 94.6 | 92.8 | 99.3 | 95.2 | No phytotoxicity |
| Example 2.1 (17% microemulsion) | 255 | 100 | 100 | 100 | 100 | No phytotoxicity |
| Example 2.3 (14% microemulsion) | 131.25 | 92.9 | 94.5 | 99.2 | 94.9 | No phytotoxicity |
| Example 2.1 (17% microemulsion) | 262.5 | 100 | 100 | 100 | 100 | No phytotoxicity |
| Example 2.4 (17% microemulsion) | 127.5 | 95.1 | 93.8 | 95.5 | 94.7 | No phytotoxicity |
| | 255 | 100 | 100 | 100 | 100 | No phytotoxicity |
| Example 3.1 (27% aqueous emulsion) | 405 | 94.8 | 93.4 | 95.6 | 97.3 | No phytotoxicity |
| Example 2.4 (17% microemulsion) | 810 | 100 | 100 | 100 | 100 | No phytotoxicity |
| Example 3.2 (3% aqueous emulsion) | 45 | 95.6 | 96.2 | 97.7 | 98.2 | No phytotoxicity |
| | 90 | 100 | 100 | 100 | 100 | No phytotoxicity |
| Example 7.2 (13% water-dispersible granule) | 150 | 91.1 | 88.7 | 86.5 | 90.3 | No phytotoxicity |
| | 300 | 96.8 | 93.7 | 92.3 | 95.6 | No phytotoxicity |
| Example 4.1 (35% suspension) | 525 | 94.1 | 92.7 | 93.2 | 93.1 | No phytotoxicity |
| | 1050 | 100 | 100 | 100 | 93.5 | No phytotoxicity |

TABLE 30-continued

Weed control efficiency of the herbicides of the present invention in wheat fields

| agents | Dosage (g a.i./ha) | Weed control efficiency (%) | | | | safety |
|---|---|---|---|---|---|---|
| | | *Sisymbrium sophia* | *Capsella bursa-pastoris* | *Rorippa indica* (L.) *Hiern* | *Lithospermum arvense* | |
| Example 4.2 (50% suspension) | 750 | 92.1 | 93.4 | 90.2 | 88.3 | No phytotoxicity |
| | 1500 | 100 | 100 | 98.2 | 95.3 | No phytotoxicity |
| Example 4.3 (35% suspension) | 262.5 | 90.2 | 89.1 | 92.4 | 89.7 | No phytotoxicity |
| | 525 | 96.1 | 95.3 | 97.2 | 94.3 | No phytotoxicity |
| Example 4.4 (4% suspension) | 60 | 92.3 | 94.5 | 93.3 | 92.5 | No phytotoxicity |
| | 120 | 100 | 100 | 99.0 | 94.5 | No phytotoxicity |
| Example 4.5 (22% suspension) | 330 | 99.3 | 98.2 | 95.7 | 94.1 | No phytotoxicity |
| | 660 | 100 | 100 | 100 | 100 | No phytotoxicity |
| Example 5.1 (20% dispersible oil suspension) | 300 | 95.8 | 97.2 | 98.1 | 96.2 | No phytotoxicity |
| | 600 | 100 | 100 | 100 | 100 | No phytotoxicity |
| Example 5.2 (37.5% dispersible oil suspension) | 562.5 | 94.3 | 95.6 | 94.3 | 92.9 | No phytotoxicity |
| | 1125 | 100 | 100 | 100 | 98.7 | No phytotoxicity |
| Example 5.3 (36.5% dispersible oil suspension) | 547.5 | 90.7 | 92.3 | 91.8 | 92.0 | No phytotoxicity |
| | 1095 | 100 | 100 | 100 | 97.4 | No phytotoxicity |
| Example 5.4 (6.8% dispersible oil suspension) | 51 | 96.8 | 96.9 | 97.3 | 94.5 | wheat slightly yellowed |
| | 102 | 100 | 100 | 100 | 100 | wheat severely yellowed |
| Example 5.5 (11% dispersible oil suspension) | 82.5 | 96.1 | 95.6 | 97.1 | 94.7 | No phytotoxicity |
| | 165 | 100 | 100 | 100 | 100 | No phytotoxicity |
| Example 5.6 (6% dispersible oil suspension) | 45 | 93.1 | 94.7 | 98.2 | 96.5 | No phytotoxicity |
| | 90 | 100 | 100 | 100 | 100 | No phytotoxicity |
| Example 5.7 (3.4% dispersible oil suspension) | 51 | 100 | 100 | 100 | 100 | No phytotoxicity |
| | 102 | 100 | 100 | 100 | 100 | No phytotoxicity |
| Example 6.1 (51.5% wettable powder) | 772.5 | 92.4 | 91.5 | 93.7 | 90.6 | No phytotoxicity |
| | 1545 | 100 | 100 | 100 | 95.5 | No phytotoxicity |
| Example 6.2 (33% wettable powder) | 495 | 94.5 | 92.8 | 94.6 | 92.3 | No phytotoxicity |
| | 990 | 100 | 99.8 | 98.5 | 94.7 | No phytotoxicity |
| Example 6.3 (40% wettable powder) | 300 | 100 | 100 | 100 | 95.5 | No phytotoxicity |
| | 600 | 100 | 100 | 100 | 100 | No phytotoxicity |
| Example 7.1 (3% water-dispersible granule) | 45 | 93.3 | 95.6 | 98.5 | 93.3 | No phytotoxicity |
| | 90 | 100 | 100 | 100 | 99.6 | No phytotoxicity |
| Example 7.2 (14% water-dispersible granule) | 210 | 90.2 | 94.5 | 92.3 | 93.5 | No phytotoxicity |
| | 420 | 100 | 100 | 100 | 99.1 | No phytotoxicity |
| Example 7.3 (18.5% water-dispersible granule) | 277.5 | 95.2 | 91.5 | 93.8 | 93.8 | No phytotoxicity |
| Example 7.2 (14% water-dispersible granule) | 555 | 100 | 100 | 100 | 100 | wheat leaves had slight contact spots |
| Example 7.4 (65% water-dispersible granule) | 487.5 | 94.1 | 95.6 | 97.3 | 96.3 | No phytotoxicity |
| Example 7.2 (14% water-dispersible granule) | 975 | 100 | 100 | 100 | 100 | No phytotoxicity |
| Example 7.5 (39% water-dispersible granule) | 93.6 | 95.1 | 95.7 | 93.8 | 97.2 | No phytotoxicity |
| | 187.2 | 100 | 100 | 100 | 100 | No phytotoxicity |
| dispersible oil suspension of 10% active ingredient A | 37.5 | 89.6 | 90.3 | 87.2 | 88.6 | No phytotoxicity |
| | 75 | 100 | 100 | 100 | 100 | No phytotoxicity |
| aqueous solution of 13% MCPA | 240 | 34.1 | 44.8 | 35.2 | 27.4 | No phytotoxicity |
| | 480 | 78.2 | 67.3 | 75.3 | 72.3 | No phytotoxicity |
| soluble powder of 56% MCPA-Na | 262.5 | 31.8 | 36.2 | 34.5 | 37.3 | No phytotoxicity |
| | 525 | 68.6 | 72.5 | 69.1 | 58.9 | No phytotoxicity |
| auspension of 40% MCPA-isooctyl | 367.5 | 34.8 | 36.9 | 41.2 | 38.3 | No phytotoxicity |
| | 735 | 58.9 | 66.1 | 72.2 | 65.7 | No phytotoxicity |
| aqueous solution of 750 g/L MCPA-dimethylammonium | 292.5 | 42.1 | 45.6 | 43.7 | 38.1 | No phytotoxicity |
| | 585 | 59.3 | 62.4 | 71.3 | 59.4 | No phytotoxicity |
| emulsifiable concentrate of 57% 2,4-D butyl ester | 345 | 34.6 | 42.4 | 38.6 | 33.5 | No phytotoxicity |
| | 690 | 50.2 | 53.7 | 54.3 | 55.7 | No phytotoxicity |

TABLE 30-continued

Weed control efficiency of the herbicides of the present invention in wheat fields

|  |  | Weed control efficiency (%) | | | | |
|---|---|---|---|---|---|---|
| agents | Dosage (g a.i./ha) | *Sisymbrium sophia* | *Capsella bursa-pastoris* | *Rorippa indica* (L.) *Hiern* | *Lithospermum arvense* | safety |
| emulsifiable concentrate of 50% 2,4-D isooctyl ester | 375 | 34.3 | 32.9 | 32.2 | 37.2 | No phytotoxicity |
|  | 750 | 54.9 | 63.7 | 69.4 | 65.7 | No phytotoxicity |
| emulsifiable concentrate of 200 g/l fluroxypyr | 90 | 33.1 | 35.6 | 28.9 | 21.7 | No phytotoxicity |
|  | 180 | 50.6 | 47.2 | 49.3 | 50.6 | No phytotoxicity |
| emulsifiable concentrate of 10% halauxifen-methyl | 7.5 | 65.2 | 61.3 | 42.1 | 55.0 | No phytotoxicity |
|  | 15 | 80.2 | 81.4 | 78.2 | 67.2 | No phytotoxicity |
| aqueous emulsion of 69 g/l fenothiocarb | 90 | 0 | 0 | 0 | 0 | No phytotoxicity |
|  | 180 | 0 | 0 | 0 | 0 | No phytotoxicity |
| wettable powder of 15% clodinafop | 90 | 0 | 0 | 0 | 0 | No phytotoxicity |
|  | 180 | 0 | 0 | 0 | 0 | No phytotoxicity |
| Suspension of 35% tralkoxydim | 450 | 0 | 0 | 0 | 0 | No phytotoxicity |
|  | 900 | 0 | 0 | 0 | 0 | No phytotoxicity |
| water-dispersible granule of 75% halosulfuron-methyl | 60 | 23.6 | 27.1 | 31.2 | 26.1 | No phytotoxicity |
|  | 120 | 40.1 | 30.9 | 38.2 | 37.4 | No phytotoxicity |
| dispersible oil suspension of 30 g/l mesosulfuron-methyl | 13.5 | 41.6 | 51.9 | 47.6 | 43.7 | wheat slightly yellowed |
|  | 27 | 50.6 | 61.8 | 63.7 | 77.8 | wheat severely yellowed |
| water-dispersible granule of 70% flucarbazone-sodium | 45 | 45.2 | 47.7 | 50.3 | 30.1 | No phytotoxicity |
|  | 90 | 67.2 | 66.3 | 71.2 | 50.8 | No phytotoxicity |
| Suspension of 50 g/l florasulam | 7.5 | 67.3 | 75.2 | 62.1 | 58.2 | No phytotoxicity |
|  | 15 | 80.3 | 84.3 | 72.3 | 78.2 | No phytotoxicity |
| water-dispersible granule of 7.5% pyroxsulam | 13.5 | 42.1 | 35.6 | 48.2 | 51.2 | No phytotoxicity |
|  | 27 | 82.9 | 74.1 | 88.2 | 75.3 | wheat yellowed |
| emulsifiable concentrate of 5% pinoxaden | 90 | 0 | 0 | 0 | 0 | No phytotoxicity |
|  | 180 | 0 | 0 | 0 | 0 | No phytotoxicity |
| water-dispersible granule of 40% carfentrazone | 30 | 92.3 | 91.8 | 91.2 | 78.2 | No phytotoxicity |
|  | 60 | 100 | 99.3 | 98.3 | 83.2 | wheat leaves had slight contact spots |
| emulsifiable concentrate of 10% fluoroglycofen | 60 | 90.1 | 88.2 | 89.2 | 89.0 | No phytotoxicity |
|  | 120 | 99.8 | 95.7 | 96.3 | 92.5 | wheat leaves had slight contact spots |
| soluble powder of 80% bromoxynil | 360 | 87.3 | 81.2 | 84.6 | 90.9 | No phytotoxicity |
|  | 720 | 94.5 | 97.1 | 91.9 | 92.3 | No phytotoxicity |
| emulsifiable concentrate of 25% bromoxynil octanoate | 375 | 89.3 | 91.7 | 90.3 | 91.2 | No phytotoxicity |
|  | 750 | 93.0 | 94.5 | 95.8 | 94.1 | No phytotoxicity |
| aqueous solution of 25% bentazon | 1000 | 88.8 | 87.3 | 88.4 | 81.6 | No phytotoxicity |
|  | 2000 | 92.3 | 91.4 | 93.2 | 91.7 | No phytotoxicity |
| wettable powder of 50% isoproturon | 1050 | 90.7 | 88.4 | 89.2 | 82.5 | No phytotoxicity |
|  | 2100 | 100 | 93.7 | 94.4 | 89.3 | No phytotoxicity |
| wettable powder of 25% chlorotoluron | 1500 | 83.2 | 78.4 | 81.1 | 60.3 | No phytotoxicity |
|  | 3000 | 90.1 | 87.9 | 83.5 | 72.1 | No phytotoxicity |
| suspension of 50% terbutryn | 275 | 86.7 | 89.3 | 83.2 | 50.3 | No phytotoxicity |
|  | 550 | 94.6 | 93.2 | 89.5 | 58.2 | No phytotoxicity |
| wettable powder of 40% prometryn | 450 | 90.7 | 88.2 | 91.5 | 90.1 | No phytotoxicity |
|  | 900 | 95.2 | 95.5 | 94.1 | 94.6 | No phytotoxicity |
| suspension of 48% metribuzin | 528 | 84.1 | 80.6 | 87.8 | 80..5 | No phytotoxicity |
|  | 1056 | 94.7 | 93.3 | 91.5 | 92.3 | wheat leaves had slight contact spots |
| wettable powder of 50% diflufenican | 200 | 88.2 | 89.3 | 83.5 | 78.1 | No phytotoxicity |
|  | 400 | 95.1 | 94.6 | 90.7 | 86.2 | No phytotoxicity |
| suspension of 10% picolinafen | 60 | 90.3 | 87.2 | 88.1 | 75.4 | No phytotoxicity |
|  | 120 | 93.4 | 95.6 | 90.5 | 78.2 | wheat leaves slightly whitened |
| water control (CK) | — | — | — | — | — | — |

It could be seen from the experimental results in the tables that the compositions of the invention displayed a good control effect on broad-leaved weeds in wheat fields, and the active ingredient A showed a significant synergistic effect with an active ingredient selected from MCPA, MCPA-Na, MCPA-isooctyl, MCPA-dimethylammonium, 2,4-D butyl ester, 2,4-D isooctyl ester, fluroxypyr, halauxifen-methyl, isoproturon, diflufenican, picolinafen, carfentrazone, fluoroglycofen, halosulfuron-methyl, metribuzin, prometryn, terbuthylazine, florasulam, bentazon, bromoxynil, and bromoxynil octanoate, and the synergistic effect was particularly evident on *Sisymbrium Sophia, Capsella bursa-pastoris*. The compositions were safe to wheat. In single agent tests, a water-dispersible granule of 40% carfentrazone, an emulsifiable concentrate of 10% fluoroglycofen, a suspension of 48% metribuzin, and a suspension of 10% picolinafen exhibited slight phytotoxicity to wheats at a high dosage. The active ingredient A and an active ingredient selected from fenothiocarb, clodinafop(clodinafop-propargyl), tralkoxydim, mesosulfuron-methyl, flucarbazone-sodium, pyroxsulam, pinoxaden, and chlorotoluron exhibited significant herbicidal complementation on broad-leaved weeds. As an agent for treating stems and leaves, an emulsifiable concentrate, suspoemulsion, suspension, dispersible oil suspension or water-dispersible granule showed good convenience in application process and outstanding control effect on weeds, and greatly improved the safety for crops.

2) Experiments for the effect on ALS-resistant *Sisymbrium Sophia*

*Sisymbrium sophia* seeds for the test, which were resistant to tribenuron, were collected from Gaocheng, Shijiazhuang, Hebei Province in 2014. The agent of Example 1.3, Example 2.1, Example 3.1, Example 5.1, and Example 5.2 were applied. Experimental methods: the weed seeds were all subjected to germination, and the pre-treated weed seeds for the test were evenly spread on the surface of the soil. The weeds were thinned out prior to application of the agents to reach a final singling of 30 weed strains in each pot. 4 pots were employed for each treatment. The agents were sprayed on the stems and leaves of the weeds, the number of dead weeds was investigated, and the control efficiency on weed strains (hereafter referred to weed control efficiency) was calculated (the weed control efficiency in the table was an average value of 4 replicates). The test results were counted after 45 days of the test and were shown in Table 31.

Weed control efficiency =

$$\frac{\text{number of weed strains in the water control area} - \text{number of weed strains in the area treated with agents}}{\text{number of weed strains in the water control area}}$$

TABLE 31

Effect on ALS-resistant *Sisymbrium Sophia*

| Agents | Dosage (g a.i./ha) | Control effect on *Sisymbrium Sophia* (%) |
|---|---|---|
| Example 1.3 (27.5% emulsifiable concentrate) | 412.5 | 100 |

TABLE 31-continued

Effect on ALS-resistant *Sisymbrium Sophia*

| Agents | Dosage (g a.i./ha) | Control effect on *Sisymbrium Sophia* (%) |
|---|---|---|
| Example 2.1 (17% microemulsion) | 127.5 | 100 |
| Example 3.1 (27% aqueous emulsion) | 405 | 100 |
| Example 3.2 (3% aqueous emulsion) | 45 | 100 |
| Example 5.1 (20% dispersible oil suspension) | 300 | 100 |
| Example 5.2 (37.5% dispersible oil suspension) | 562.5 | 100 |
| wettable powder of 10% tribenuron | 30 | 0 |
| Water control (CK) | — | — |

The application of the agent in Example 1.3, 2.1, 3.1, 3.2, 5.1 or 5.2 was effective in controlling *Sisymbrium sophia* which was target-resistant to tribenuron, and no cross-resistance between the agent and tribenuron was observed.

3) Exemplary experiments for controlling weeds in wheat fields by the compositions of the present invention In 2014, exemplary pilot projects were conducted in 25 pilot sites of Shijiazhuang of Hebei Province, Taian of Shandong Province, Zhumadian of Henan Province, Luohe of Henan province and Siyang of Jiangsu Province. Wheat varieties in the different pilot sites were shown in Table 32.

TABLE 32

Wheat varieties in the different pilot sites

| Pilot sites | Wheat varieties | Type |
|---|---|---|
| Shijiazhuang | Gaoyou 5766 | Hard white wheat |
| Tai'an | Yanmai 20 | Hard white wheat |
| Zhumadian | Zhoumai 26 | Hard white wheat |
| Luohe | Yumai 18 | Hard white wheat |
| Siyang | Yangmai 158 | Hard red wheat |

Experimental methods: In the stage of 3 leaves and 1 core of the wheat and 3-5 leaves of the weed, the agent was evenly sprayed on stems and leaves through a manual sprayer, wherein the amount of added water was 15 kg/667 m$^2$, the specific tested agents and dosage thereof were shown in Table 33. The area of the pilot site was 50 square meters, and each treatment was repeated for 4 times. The weed control efficiency after 45 days of application was shown in Table 33, and the safety of wheat was shown in Table 34.

Weed control efficiency (%) =

$$\frac{\text{number of weed strains in the water control area} - \text{number of weed strains in the area treated with agents}}{\text{number of weed strains in the water control area}}$$

TABLE 33 controlling effect in pilot sites

| Agents | dosage (g a.i./ha) | Weed control efficiency in different pilot sites (%) | | | | |
|---|---|---|---|---|---|---|
| | | Shijiazhuang | Tai'an | Zhumadian | luohe | Siyang |
| Example 1.1 (3% emulsifiable concentrate) | 45 | 94.2 | 93.6 | 92.1 | 90.8 | 89.6 |

TABLE 33-continued controlling effect in pilot sites

| Agents | dosage (g a.i./ha) | Weed control efficiency in different pilot sites (%) | | | | |
|---|---|---|---|---|---|---|
| | | Shijiazhuang | Tai'an | Zhumadian | luohe | Siyang |
| Example 1.3 (27.5% emulsifiable concentrate) | 412.5 | 94.7 | 93.5 | 94.3 | 88.9 | 92.4 |
| Example 4.1 (35% suspension) | 525 | 95.9 | 92.4 | 91.7 | 88.9 | 88.7 |
| Example 4.2 (50% suspension) | 750 | 93.2 | 96.2 | 93.8 | 91.7 | 92.1 |
| Example 4.3 (35% suspension) | 262.5 | 90.7 | 87.4 | 84.3 | 82.4 | 90.4 |
| Example 4.4 (4% suspension) | 60 | 92.8 | 91.5 | 89.0 | 88.1 | 86.7.8 |
| Example 5.1 (20% dispersible oil suspension) | 300 | 94.6 | 92.1 | 88.4 | 89.4 | 86.5 |
| Example 5.2 (37.5% dispersible oil suspension) | 300 | 99.2 | 96.8 | 95.5 | 94.1 | 94.3 |
| Example 6.1 (51.5% wettable powder) | 772.5 | 88.3 | 89.4 | 82.6 | 87.7 | 90.3 |
| Example 6.2 (33% wettable powder) | 495 | 89.9 | 90.3 | 87.4 | 90.6 | 86.5 |
| Example 7.2 (14% water-dispersible granule) | 150 | 93.2 | 94.6 | 91.2 | 90.5 | 91.2 |
| Dispersible oil suspension of 10% active ingredient A | 37.5 | 90.2 | 84.5 | 86.9 | 90.3 | 90.1 |
| Emulsifiable concentrate of 10% fluoroglycofen | 60 | 90.3 | 91.5 | 87.4 | 82.3 | 86.4 |
| Soluble powder of 80% bromoxynil | 360 | 90.7 | 78.4 | 79.8 | 81.2 | 73.2 |
| Emulsifiable concentrate of 25% bromoxynil octanoate | 375 | 88.2 | 90.6 | 82.4 | 81.0 | 78.1 |
| Aqueous solution of 25% bentazon | 1000 | 84.3 | 90.5 | 86.1 | 78.4 | 80.4 |
| Wettable powder of 50% isoproturon | 1050 | 81.4 | 76.1 | 84/6 | 80.5 | 88.3 |
| Wettable powder of 25% chlorotoluron | 1500 | 80.1 | 74.7 | 76.8 | 73.4 | 79.2 |
| Suspension of 50% terbutryn | 275 | 74.5 | 69.8 | 77.6 | 78.4 | 80.3 |
| Wettable powder of 40% prometryn | 450 | 84.6 | 82.1 | 89.7 | 85.6 | 87.3 |
| Suspension of 48% metribuzin | 528 | 78.2 | 82.3 | 85.6 | 73.5 | 74.6 |
| Wettable powder of 50% diflufenican | 200 | 82.6 | 81.3 | 86.7 | 88.4 | 85.4 |
| 10% picolinafen suspension | 60 | 89.2 | 83.2 | 82.9 | 90.5 | 76.9 |
| Water control (CK) | — | — | — | — | — | — |

TABLE 34

Safety of the wheat in the pilot sites

| Agents | Dosage (g a.i./ha) | Safety of the wheat | | | | |
|---|---|---|---|---|---|---|
| | | Shijiazhuang | Tai'an | Zhumadian | Luohe | Siyang |
| Example 1.1 (3% emulsifiable concentrate) | 45 | safety | safety | Safety | safety | Safety |
| Example 1.3 (27.5% emulsifiable concentrate) | 412.5 | safety | safety | Safety | safety | Safety |
| Example 4.1 (35% suspension) | 525 | safety | safety | Safety | safety | Safety |
| Example 4.2 (50% suspension) | 750 | safety | safety | Safety | safety | Safety |
| Example 4.3 (35% suspension) | 262.5 | safety | safety | Safety | safety | Safety |
| Example 4.4 (4% suspension) | 60 | safety | safety | Safety | safety | Safety |
| Example 5.1 (20% dispersible oil suspension) | 300 | safety | safety | Safety | safety | Safety |
| Example 5.2 (37.5% dispersible oil suspension) | 300 | safety | safety | Safety | safety | Safety |
| Example 6.1 (51.5% wettable powder) | 772.5 | safety | safety | Safety | safety | Safety |
| Example 6.2 (33% wettable powder) | 495 | safety | safety | Safety | safety | Safety |
| Example 7.2 (14% water-dispersible granule) | 150 | safety | safety | Safety | safety | Safety |
| Dispersible oil suspension of 10% active ingredient A | 37.5 | safety | safety | Safety | safety | Safety |
| Emulsifiable concentrate of 10% fluoroglycofen | 60 | safety | safety | Safety | safety | Safety |

TABLE 34-continued

Safety of the wheat in the pilot sites

| Agents | Dosage (g a.i./ha) | Safety of the wheat | | | | |
|---|---|---|---|---|---|---|
| | | Shijiazhuang | Tai'an | Zhumadian | Luohe | Siyang |
| Soluble powder of 80% bromoxynil | 360 | safety | safety | Safety | safety | Safety |
| Emulsifiable concentrate of 25% bromoxynil octanoate | 375 | safety | safety | Safety | safety | Safety |
| Aqueous solution of 25% bentazon | 1000 | safety | safety | Safety | safety | Safety |
| Wettable powder of 50% isoproturon | 1050 | safety | safety | Safety | safety | Safety |
| Wettable powder of 25% chlorotoluron | 1500 | safety | safety | Safety | safety | Safety |
| Suspension of 50% terbutryn | 275 | safety | safety | Safety | safety | Safety |
| Wettable powder of 40% prometryn | 450 | safety | safety | Safety | safety | Safety |
| Suspension of 48% metribuzin | 528 | safety | safety | Safety | slight contact spots | safety |
| Wettable powder of 50% diflufenican | 200 | safety | safety | Safety | Safety | safety |
| Suspension of 10% picolinafen | 60 | safety | safety | wheat slightly whitened | Safety | safety |
| Water control (CK) | — | — | — | — | — | — |

Notes: the types of weed communities in each of the pilot sites: Shijiazhuang: *Sisymbrium sophia*+*Capsella bursa-pastoris*; Tai'an: *Sisymbrium sophia*+*Capsella* bursa-*pastoris*+*Catchweed*; Zhumadian: *Capsella bursa-pastoris*+*Sisymbrium sophia*+*Catchweed*+Chickweed; Luohe: *Capsella bursa-pastoris*+*Catchweed*+*Euphorbia helioscopia*; Siyang: *Capsella bursa-pastoris*+*Myosoton aquaticum*+*Catchweed*+*Cardamine hirsute*+Vetch.

After extensive experiments and researches, the present inventors surprisingly found that a 4-benzoylpyrazole herbicide displayed a surprising and unexpected synergistic effect when applied in combination with an active ingredient B, in the control of broad-leaved weeds for postemergence application in wheat fields, especially on cruciferous weeds, such as *Sisymbrium sophia, Capsella bursa-pastoris, Rorippa* indica (L.) Hiern, *Cardamine hirsute* and the like. And no cross resistance was observed on the weeds which were resistant to an ALS inhibitor or an PPO inhibitor. The two ingredients had been shown to be more effective in combination than when applied individually, indicating a significant synergistic effect was displayed. And in the meantime, the application rate could be reduced, the safety for the crops was improved, and the pollution of environment was reduced. Moreover, such rationally compounding of active ingredients reduced agricultural costs and had good prospects.

The herbicidal compositions were not only effective in controlling typical weeds such as non-resistant *Sisymbrium sophia, Capsella bursa-pastoris, Rorippa* indica (L.) Hiern, *Cardamine hirsuta, Catchweed,* Chickweed, *Myosoton aquaticum, Lithospermum arvense, Silene conoidea, Euphorbia helioscopia,* Vetch, *Geranium carolinianum, Veronica polita, Lamium amplexicaule, Chenopodiaceae, Cirsium setosum,* and *Polygonum aviculare* etc., and could also effectively control cruciferous weeds (e.g., *Sisymbrium Sophia, Capsella bursa-pastoris, Rorippa* indica (L.) Hiern and *Cardamine hirsuta* etc.), which have a cross resistance resulted from target resistance to an ALS inhibitor which was commonly used in wheat fields, such as tribenuron, bensulfuron-methyl, florasulam and the like.

The invention claimed is:

1. A synergistic herbicidal composition, comprising an active ingredient A and an active ingredient B, each in an herbicidally effective amount,
wherein, the active ingredient A is

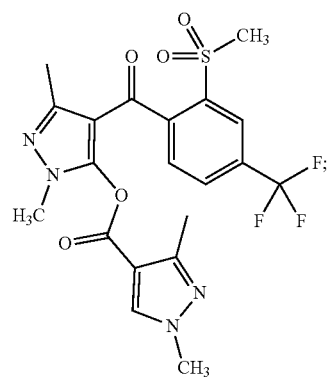 [SMILES: Cc1nn(C)cc1C(=O)Oc1c(C(=O)c2ccc(C(F)(F)F)cc2S(C)(=O)=O)c(C)nn1C]

the active ingredient B is one or more compounds selected from:
 1) a phenoxycarboxylic acid;
 2) a pyridinecarboxylic acid;
 3) a benzoic acid;
 4) a hydroxybenzonitrile;
 5) isoproturnon or chlorotoluron;
 6) a pyridine;
 7) a triazolinone;
 8) a diphenyl ether;
 9) an acetamide;
 10) an aryloxyphenoxypropionate;
 11) a cyclohexanedione;
 12) a sulfonylurea;
 13) a triazine;
 14) a sulfonamide;
 15) a phenylpyrazoline; and
 16) bentazon.

2. The synergistic herbicidal composition according to claim 1, wherein the active ingredient B is one or more compounds selected from a group consisting of 2-methyl-4-chlorophenoxy acetic acid (MCPA), MCPA-Na, MCPA-isooctyl, 2,4-Dichlorophenoxyacetic acid butyl ester (2,4-D butyl ester), 2,4-D isooctyl ester, fluroxypyr, fluroxypr-mepthyl, halauxifen-methyl, isoproturon, diflufenican, picolinafen, carfentrazone, fluoroglycofen, fenothiocarb, clodinafop, clodinafop-propargyl, tralkoxydim, halosulfuron-methyl, mesosulfuron-methyl, flucarbazone-sodium, metribuzin, prometryn, terbutryn, florasulam, pyroxsulam, pinoxaden, bentazon, bromoxynil, bromoxynil octanoate, and chlorotoluron.

3. The synergistic herbicidal composition according to claim 1, wherein the weight ratio of the active ingredient A to the active ingredient B is 1-100: 1-100.

4. The synergistic herbicidal composition according to claim 1, wherein the weight ratio of the active ingredient A to the active ingredient B is 1-50: 1-50.

5. The synergistic herbicidal composition according to claim 1, wherein the weight ratio of the active ingredient A to the active ingredient B is 1-20: 1-20.

6. The synergistic herbicidal composition according to claim 1, wherein, the active ingredients A and B together account for 1-95% of the total weight of the synergistic herbicidal composition.

7. The synergistic herbicidal composition according to claim 1, wherein the synergistic herbicidal composition is an emulsifiable concentrate, a suspension, a microemulsion, a suspoemulsion, an aqueous emulsion, a dispersible oil suspension, a wettable powder or a water-dispersible granule.

8. The synergistic herbicidal composition according to claim 1, further comprising a safener C.

9. The synergistic herbicidal composition according to claim 8, wherein the safener C is one or more compounds selected from a group consisting of mefenpyr-diethyl, cloquintocet-methyl, isoxadifen-ethyl, cyprosulfamide, naphthalic anhydride (NA), Dichlormid, R-28725 (3-Dichloroacetyl-2,2-dimethyl-1,3-oxazolidine), AD-67 (4-Dichloroacetyl-1-oxa-4-azaspiro[4.5]decane), CGA-154281 (Benoxacor), CGA-43089 (Cyometyinil), Hoe-70542 (Fenchlorazole), Fenclorim, Flurazole, BAS-145138 (5-Dichloroacetyl-3,3,6-trimethyl-9-oxo-1,5-diazabicyclo[4.3.0]nonane), MON-13900 (Furilazole), quinoline derivatives, 2,4-D and gibberellin.

10. The synergistic herbicidal composition according to claim 1, wherein; the active ingredient B is one or more compounds selected from:
1) the phenoxycarboxylic acid is selected from a group consisting of 2-methyl-4-chlorophenoxy acetic acid (MCPA), MCPA-thioethyl, MCPB, mecoprop, MCPA-Na, MCPA-isooctyl, 2,4-dichlorophenoxyacetic acid (2,4-D), 2,4-D butyl ester, 2,4-D isooctyl ester, 2,4-DB, and 2-(2,4-Dichlorophenoxy)propionic acid;
2) the pyridinecarboxylic acid is selected from a group consisting of fluroxypyr, fluroxypr-mepthyl, halauxifen-methyl, triclopyr, and clopyralid;
3) the benzoic acid is dicamba;
4) the hydroxybenzonitrile is selected from a group consisting of bromoxynil, bromoxynil octanoate, and ioxynil;
5) isoproturon or chlorotoluron;
6) the pyridine is diflufenican or picolinafen;
7) the triazolinone is carfentrazone;
8) the diphenyl ether is fluoroglycofen;
9) the acetamide is selected from a group consisting of acetochlor, flufenacet, mefenacet, metolachlor, and napropamid;
10) the aryloxyphenoxypropionate is selected from a group consisting of fenothiocarb, clodinafop, and clodinafop-propargyl;
11) the cyclohexanedione is tralkoxydim;
12) the sulfonylurea is selected from a group consisting of tribenuron, bensulfuron-methyl, thifensulfuron, halosulfuron-methyl, mesosulfuron-methyl, sulfosulfuron, propoxycarbazone, and flucarbazone-sodium;
13) the triazine is selected from a group consisting of metribuzin, prometryn, and terbutryn;
14) the sulfonamide is selected from a group consisting of florasulam, flumetsulam, and pyroxsulam; and
15) the phenylpyrazoline is pinoxaden.

11. The synergistic herbicidal composition according to claim 1, wherein the active ingredient B is MCPA-dimethylammonium.

12. The synergistic herbicidal composition according to claim 1, wherein, the active ingredients A and B together account for 10-80% of the total weight of the synergistic herbicidal composition.

13. A method for controlling a noxious weed which comprises a step of applying an herbicidally effective amount of the synergistic herbicidal composition according to claim 1 to the noxious weed or the locus thereof.

14. The method according to claim 13, wherein the noxious weed is a broad-leaved weed.

15. The method according to claim 13, wherein the noxious weed is a cruciferous weed.

16. The method according to claim 13, wherein the noxious weed is selected from a group consisting of *Sisymbrium sophia*, *Capsella* bursa-*pastoris*, *Rorippa indica* (L.) Hiern, *Cardamine hirsuta*, Catchweed, Chickweed, *Myosoton aquaticum*, *Lithospermum arvense*, *Silene conoidea*, *Euphorbia helioscopia*, Vetch, *Geranium carolinianum*, *Veronica polita*, *Lamium amplexicaule*, Chenopodiaceae, *Cirsium setosum*, *Polygonum aviculare*, and *Alopecurus japonicus*.

* * * * *